(12) United States Patent
Carron et al.

(10) Patent No.: US 10,945,635 B2
(45) Date of Patent: Mar. 16, 2021

(54) NEARLY ISOTROPIC DIPOLE ANTENNA SYSTEM

(71) Applicant: Rock West Medical Devices, LLC, San Juan Capistrano, CA (US)

(72) Inventors: Neal Jay Carron, Goleta, CA (US); Thomas Eugene Old, Santa Barbara, CA (US); Donald Gordon Pritchett, Santa Barbara, CA (US); John Christopher Baker, Santa Barbara, CA (US)

(73) Assignee: Rock West Medical Devices, LLC, San Juan Capistrano, CA (US)

( * ) Notice: Subject to any disclaimer, the term of this patent is extended or adjusted under 35 U.S.C. 154(b) by 1145 days.

(21) Appl. No.: 14/520,219

(22) Filed: Oct. 21, 2014

(65) Prior Publication Data

US 2015/0112189 A1    Apr. 23, 2015

Related U.S. Application Data

(60) Provisional application No. 61/894,242, filed on Oct. 22, 2013.

(51) Int. Cl.
    *A61B 5/07*     (2006.01)
    *A61B 5/06*     (2006.01)
    *A61B 5/00*     (2006.01)

(52) U.S. Cl.
    CPC .............. *A61B 5/073* (2013.01); *A61B 5/062* (2013.01); *A61B 5/065* (2013.01); *A61B 5/42* (2013.01);
    (Continued)

(58) Field of Classification Search
    CPC combination set(s) only.
    See application file for complete search history.

(56) References Cited

U.S. PATENT DOCUMENTS

| 4,742,356 | A | * | 5/1988 | Kuipers | ................ | F41G 3/225 |
| | | | | | | 342/386 |
| 5,217,449 | A | | 6/1993 | Yuda et al. | | |

(Continued)

FOREIGN PATENT DOCUMENTS

| CN | 200984246 | 12/2007 |
| CN | 101108122 A | 1/2008 |

(Continued)

OTHER PUBLICATIONS

International Search Report and Written Opinion in PCT/US2013/055461 dated Oct. 23, 2013 in 11 pages.

(Continued)

*Primary Examiner* — Christian Jang
*Assistant Examiner* — Mitchell E Alter
(74) *Attorney, Agent, or Firm* — Knobbe Martens Olson & Bear, LLP

(57) ABSTRACT

Systems and methods described herein can use near field communications to locate a radiating transmitter, such as a pill transmitter swallowed by a patient. In some embodiments, the pill transmitter can include multiple transmitting elements configured to transmit signals in an axis orthogonal with respect to each other. Further, in some embodiment, the pill transmitter can also include multiple transmitting elements in each of the three axes where the three axes may be perpendicular with respect to each other. The magnetic field emitted from the pill transmitter can be measured by the receiving antennas, for example, using principles of mutual inductance.

14 Claims, 17 Drawing Sheets

(52) U.S. Cl.
CPC .......... *A61B 5/6861* (2013.01); *A61B 5/4238* (2013.01); *A61B 5/4255* (2013.01)

(56) References Cited

U.S. PATENT DOCUMENTS

| | | | |
|---|---|---|---|
| 5,279,607 A | | 1/1994 | Schentag et al. |
| 5,964,705 A * | | 10/1999 | Truwit .................. A61B 5/055 |
| | | | 324/318 |
| 6,498,477 B1 | | 12/2002 | Govari et al. |
| 6,929,636 B1 | | 8/2005 | von Alten |
| 6,950,690 B1 | | 9/2005 | Meron et al. |
| 7,048,716 B1 * | | 5/2006 | Kucharczyk ...... A61M 25/0043 |
| | | | 600/411 |
| 7,109,933 B2 | | 9/2006 | Ito et al. |
| 7,354,398 B2 | | 4/2008 | Kanazawa |
| 7,359,765 B2 | | 4/2008 | Varvarelis et al. |
| 7,382,263 B2 | | 6/2008 | Danowski et al. |
| 7,511,733 B2 | | 3/2009 | Takizawa et al. |
| 7,596,403 B2 | | 9/2009 | Horn |
| 7,761,134 B2 | | 7/2010 | Horn et al. |
| 7,775,971 B2 | | 8/2010 | Fujimori et al. |
| 7,796,043 B2 | | 9/2010 | Euliano et al. |
| 7,797,033 B2 | | 9/2010 | D'Andrea et al. |
| 7,801,586 B2 | | 9/2010 | Muratayev et al. |
| 7,822,463 B2 | | 10/2010 | Meron et al. |
| 7,864,007 B2 | | 1/2011 | Fujimori et al. |
| 7,896,805 B2 | | 3/2011 | Gilad et al. |
| 7,918,786 B2 | | 4/2011 | Kawano et al. |
| 7,998,065 B2 | | 8/2011 | Avni |
| 8,052,595 B2 | | 11/2011 | Minai |
| 8,147,482 B2 | | 4/2012 | Shimizu et al. |
| 8,203,434 B2 | | 6/2012 | Yoshida |
| 8,335,556 B2 | | 12/2012 | Uchiyama et al. |
| 8,348,835 B2 | | 1/2013 | Fujimori |
| 8,353,821 B2 | | 1/2013 | Segawa |
| 8,419,614 B2 | | 4/2013 | Fujita |
| 8,423,122 B2 | | 4/2013 | Steinberg et al. |
| 8,439,822 B2 | | 5/2013 | Shigemori et al. |
| 8,446,332 B2 | | 5/2013 | Homan |
| 8,512,241 B2 | | 8/2013 | Bandy et al. |
| 8,518,022 B2 | | 8/2013 | Trovato et al. |
| 8,591,403 B2 | | 11/2013 | Yoshida |
| 8,597,278 B2 | | 12/2013 | Trovato et al. |
| 8,597,279 B2 | | 12/2013 | Dijksman et al. |
| 8,622,909 B1 | | 1/2014 | O'Ruanaidh et al. |
| 8,808,165 B2 | | 8/2014 | Okabe |
| 8,846,040 B2 | | 9/2014 | Imran |
| 8,852,172 B2 | | 10/2014 | Dijksman et al. |
| 8,900,142 B2 | | 12/2014 | Old et al. |
| 8,911,351 B2 | | 12/2014 | Koide |
| 8,911,425 B2 | | 12/2014 | Dijksman et al. |
| 8,932,221 B2 | | 1/2015 | Colliou et al. |
| 8,974,373 B2 | | 3/2015 | Hasegawa et al. |
| 9,039,606 B2 | | 5/2015 | Uchiyama et al. |
| 9,078,579 B2 | | 7/2015 | Gilad et al. |
| 9,131,842 B2 | | 9/2015 | Old et al. |
| 9,186,040 B2 | | 11/2015 | Tanaka |
| 9,270,025 B2 | | 2/2016 | Robertson et al. |
| 9,486,127 B2 | | 11/2016 | Igarashi et al. |
| 9,743,880 B1 | | 8/2017 | Euliano et al. |
| 9,757,009 B2 | | 9/2017 | Sato et al. |
| 9,814,374 B2 | | 11/2017 | Kirma et al. |
| 10,045,713 B2 | | 8/2018 | Old et al. |
| 2002/0167313 A1 | | 11/2002 | Taimisto |
| 2002/0173718 A1 | | 11/2002 | Frisch et al. |
| 2003/0181788 A1 | | 9/2003 | Yokoi et al. |
| 2003/0191430 A1 | | 10/2003 | D'Andrea et al. |
| 2004/0068204 A1 | | 4/2004 | Imran et al. |
| 2004/0143182 A1 | | 7/2004 | Kucera et al. |
| 2004/0181127 A1 | | 9/2004 | Matsumoto et al. |
| 2004/0210131 A1 | | 10/2004 | Fukuda et al. |
| 2005/0064815 A1 * | | 3/2005 | Kanazawa ......... A61B 1/00016 |
| | | | 455/41.1 |
| 2005/0104776 A1 | | 5/2005 | Anderson |
| 2005/0151696 A1 * | | 7/2005 | Govari ................. H01Q 7/00 |
| | | | 343/788 |
| 2006/0004257 A1 | | 1/2006 | Gilad et al. |
| 2006/0155174 A1 | | 7/2006 | Glukhovsky et al. |
| 2007/0213659 A1 | | 9/2007 | Trovato et al. |
| 2007/0282252 A1 | | 12/2007 | Stukanov |
| 2008/0009711 A1 | | 1/2008 | Govari et al. |
| 2008/0063703 A1 | | 3/2008 | Gross et al. |
| 2008/0269664 A1 | | 10/2008 | Trovato et al. |
| 2008/0312501 A1 | | 12/2008 | Hasegawa et al. |
| 2009/0131784 A1 * | | 5/2009 | Betesh ............... A61B 1/00016 |
| | | | 600/424 |
| 2009/0192348 A1 | | 7/2009 | Nishino |
| 2009/0292167 A1 | | 11/2009 | Kimoto |
| 2010/0016667 A1 | | 1/2010 | Segawa et al. |
| 2010/0016672 A1 | | 1/2010 | Segawa et al. |
| 2010/0049012 A1 | | 2/2010 | Dijksman et al. |
| 2010/0222670 A1 | | 9/2010 | Demierre et al. |
| 2010/0326703 A1 | | 12/2010 | Gilad et al. |
| 2010/0331827 A1 | | 12/2010 | Shimizu |
| 2011/0071385 A1 | | 3/2011 | Bouchoucha |
| 2011/0125007 A1 | | 5/2011 | Steinberg et al. |
| 2011/0148714 A1 | | 6/2011 | Schantz et al. |
| 2011/0184235 A1 | | 7/2011 | Schostek et al. |
| 2011/0319749 A1 | | 12/2011 | Wang et al. |
| 2012/0116358 A1 | | 5/2012 | Dijksman et al. |
| 2012/0149981 A1 | | 6/2012 | Khait et al. |
| 2012/0277529 A1 | | 11/2012 | Popescu |
| 2012/0296165 A1 | | 11/2012 | Segawa |
| 2013/0204233 A1 | | 8/2013 | Zou et al. |
| 2013/0230094 A1 * | | 9/2013 | Eliezer .................. H04H 40/27 |
| | | | 375/238 |
| 2013/0237774 A1 | | 9/2013 | Schentag et al. |
| 2013/0331649 A1 | | 12/2013 | Khait et al. |
| 2014/0051949 A1 | | 2/2014 | Old et al. |
| 2014/0058221 A1 | | 2/2014 | Old et al. |
| 2014/0135698 A1 | | 5/2014 | Zou et al. |
| 2014/0149981 A1 | | 5/2014 | Luxenberg et al. |
| 2014/0180005 A1 | | 6/2014 | Igarashi et al. |
| 2014/0180040 A1 | | 6/2014 | Fujimori et al. |
| 2014/0357949 A1 | | 12/2014 | Wilson |
| 2015/0011874 A1 | | 1/2015 | Amoako-Tuffour et al. |
| 2015/0031954 A1 | | 1/2015 | Kimoto et al. |
| 2015/0112189 A1 | | 4/2015 | Old et al. |
| 2015/0141967 A1 | | 5/2015 | Pardoel et al. |
| 2015/0196229 A1 | | 7/2015 | Old et al. |
| 2016/0135668 A1 | | 5/2016 | Gat et al. |
| 2017/0215713 A1 | | 8/2017 | Kimura et al. |
| 2017/0360283 A1 | | 12/2017 | Kimura et al. |

FOREIGN PATENT DOCUMENTS

| | | |
|---|---|---|
| CN | 101352343 | 1/2009 |
| CN | 100588378 | 2/2010 |
| CN | 105559737 A | 5/2016 |
| CN | 107134634 A | 9/2017 |
| EP | 1 440 659 | 7/2004 |
| EP | 1 502 545 A1 | 2/2005 |
| EP | 1502545 A1 | 2/2005 |
| EP | 2572627 A1 | 3/2013 |
| IL | 175930 B | 12/2012 |
| JP | H4-180736 | 6/1992 |
| JP | 2004-298560 | 10/2004 |
| JP | 2005-052637 A | 3/2005 |
| JP | 2005-130943 | 5/2005 |
| JP | 2007-024892 | 2/2007 |
| JP | 2007075261 A | 3/2007 |
| JP | 4360730 B2 | 11/2009 |
| JP | 4533635 B2 | 9/2010 |
| JP | 4961898 B2 | 6/2012 |
| WO | WO 2007/074445 | 7/2007 |
| WO | WO 2007/110270 | 10/2007 |
| WO | WO 2008/120156 | 10/2008 |
| WO | WO 2009/063375 | 5/2009 |
| WO | WO 2010/004555 | 1/2010 |
| WO | WO 2012/056323 A2 | 5/2012 |
| WO | WO 2014/028902 | 2/2014 |
| WO | WO 2014028902 | 2/2014 |
| WO | WO 2014/102791 A2 | 7/2014 |

(56) References Cited

FOREIGN PATENT DOCUMENTS

| WO | WO 2015/061343 | 4/2015 |
|---|---|---|
| WO | WO 2015/146610 A1 | 10/2015 |
| WO | WO 2016/154209 | 9/2016 |
| WO | WO 2016154209 | 9/2016 |

OTHER PUBLICATIONS

Hiroz, et al., Colonic Movements in Healthy Subjects as Monitored by a Magnet Tracking System, Neurogastroenterol Motil (2009) 21, in 10 pages.
Alonso, et al., Enabling Robotic Functions in an Endoscopic Capsule, Universitat de Barcelona, May 27, 2010 in 19 pages.
International Search Report and Written Opinion in PCT/US2014/061611 dated Jan. 14, 2015 in 12 pages.
U.S. Appl. No. 1/047,554, filed Jul. 27, 2018, Old et al.
International Search Report and Written Opinion in PCT/US2016/023595 dated Jun. 20, 2016 in 16 pages.
Fassov, J. et al., "A randomized, controlled study of small intestinal motility in patients treated with scral nerve stimulation for irritable bowel syndrome," BioMed Central, Dec. 6, 2013, in 8 pages. http://www.biomedcentral.com/1471-230X/14/111.
Haase, A.M. et al., "*Pilot study trialling a new ambulatory method for the clinical assessment of regional gastrointestinal transit using multiple electromagnetic capsules,*" Neurogastroenterology & Mobility, Oct. 27, 2014, in 9 pages.
Hosseini, S. "*Design, Fabrication and Control of a Magnetic Capsule Robot for the Human Esophagus,*" A thesis presented to the University of Waterloo, Ontario, Canada, 2009, in 115 pages.
"*IntelliCap®—Electronic Capsule for Personalized Oral Controlled Release,*" MediMetrics, Apr. 18, 2012, in 8 pages.
Lambert, A. et al. "*Autonomous Telemetric Capsule to Explore the Small Bowel,*" Medical and Biological Engineering and Computing, vol. 29, Issue 2, pp. 191-196, Mar. 1, 1991, in 6 pages.
McCaffrey, C. et al., "*Swallowable-Capsule Technology,*" Tyndall National Research Institute, IEEE CS, Jan.-Mar. 2008, in 7 pages.
Tebrean, B. et al., "*Novel Drug Delivery Systems—Method Review,*" Acta Electrotehnica vol. 52, No. 1, Jan. 21, 2011, in 7 pages.
Trafton, A., "*Successful Human Tests for First Wirelessly Controlled Drug-Delivery Chip,*" MIT News, Feb. 16, 2012, in 3 pages.
Yadav, N., "Intelligent Pills," Pharmainfo.net, Aug. 12, 2009, in 12 pages. http://www.pharmainfo.net/nikkuyadav/publications/intelligentpills.
Chen, et al. "Active Atuation System of Wireless Capsule Endoscope Based on Magnetic Field." Robotics and Biomimetics, 2007. ROBIO 2007. IEEE International Conference on IEEE, 2007 (Chen).
Khan, Ahsan Noor, "Multi-antenna systems for wireless capsule endoscopy," School of Electrical Engineering, Aalto University, Sep. 9, 2016 in 54 pages.
Maloney, Dan, "Swallow the Doctor—The Present and Future of Robots Inside Us," Hackaday.com, dated Nov. 30, 2015 in 5 pages.
Al-Rawhani, et al., "Wireless Fluorescence Capsule for Endoscopy Using Single Photon-Based Detection," Nature.com/scientificreports/, Scientific Reports, Article No. 5:18591, dated Jun. 5, 2015 in 9 pages.
Vittal, Harsha, et al., "Capsule Endoscopy," South Bay Gastroenterology, Given Imaging, dated 2010 in 3 pages.
Mone, Gregory, "How It Works: The Endoscope Camera in a Pill," Popular Science, dated Mar. 13, 2008 in 6 pages.
Nathan, Stuart, "Video Pill Shrinks Cancer Detection Technique," The Engineer, dated Dec. 18, 2015 in 2 pages.
St. John Providence Health System, "Capsule Endoscopy," dated 2015 in 2 pages.
Ghoshal, Uday C., "Capsule Endoscopy: A New Era of Gastrointestinal Endoscopy, Endoscopy of GI Tract" Associate Prof. Somchai Amornyotin (Ed.), InTech, DOI: 10.5772/52732. dated 2013 in 14 pages. Available from: https://www.intechopen.com/books/endoscopy-of-gi-tract/capsule-endoscopy-a-new-era-of-gastrointestinal-endoscopy.
Beccani, Marco, et al., "Systematic Design of Medical Capsule Robots," Vanderbilt.edu, StormLab, dated Jul. 2015, in 8 pages.
Arefin, Shamsul, MD, et al., "Integration of Low-Power ASIC and MEMS Sensors for Monitoring Gastrointestinal Tract Using a Wireless Capsule System," IEEE Journal of Biomedical and Health Informatics (vol. 22, Issue 1) dated Jan. 2018 in 11 pages.
Beccani, Marco, et al., Systematic Design of Medical Capsule Robots, Vanderbilt University, IEEE Design & Test, dated Sep./Oct. 2015, pp. 98-108.
Lee, Jyung Hyun, et al., "Wireless Transmission Method for Vga Capsule Endoscopy Using Manchester Encoding," Biomed. Eng. Lett. (Oct. 28, 2013) 3: 250. https://doi.org/10.1007/s13534-013-0110-2 in 8 pages.
Given Imaging Ltd., "PillCam® Capsule Endoscopy," User Manual® Rapid v8.0 DOC-2044-02, dated Mar. 2013 in 216 pages.

\* cited by examiner

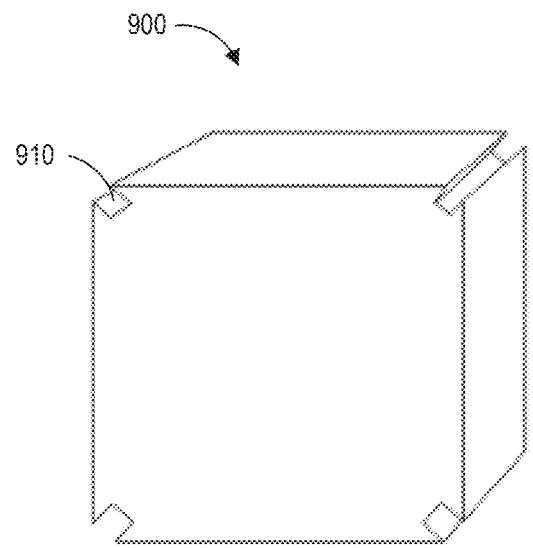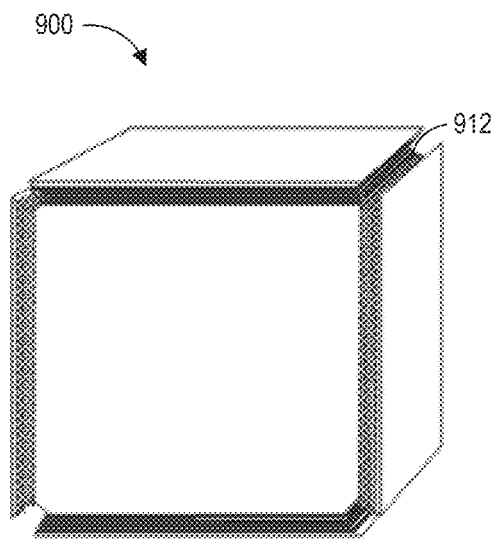
FIG. 9A  FIG. 9B
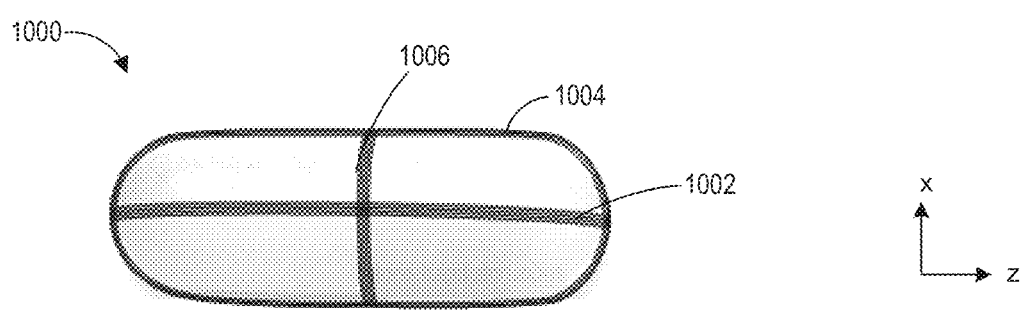
FIG. 10

NEARLY ISOTROPIC DIPOLE ANTENNA SYSTEM

RELATED APPLICATIONS

This application claims priority under 35 U.S.C. § 119(e) as a nonprovisional of U.S. Provisional Application No. 61/894,242, filed Oct. 22, 2013, titled NEARLY ISOTROPIC DIPOLE ANTENNA. This application is also related to U.S. application Ser. No. 13/969,423, filed Aug. 16, 2013, titled SYSTEM AND METHODS FOR LOCATING RELATIVE POSITIONS OF MULTIPLE PATIENT ANTENNAS and application Ser. No. 13/969,435, filed Aug. 16, 2013, titled SYSTEM AND METHODS FOR LOCATING A RADIOFREQUENCY TRANSCEIVER IN THE HUMAN BODY. The disclosures of each of the foregoing applications are hereby incorporated by reference in their entirety.

BACKGROUND

Movement of food through the human digestive tract can be obstructed or slowed for a variety of reasons. Frequently, there may be little or no pain, yet the condition may result in death if the condition is not identified and treated quickly. Reasons for gastrointestinal (GI) dismotility are numerous, including bowel strangulation, neuropathy, diverticulitis, paraplegia, diabetic gastroparesis, chemotherapy, mental conditions, and drug interaction. People of some or all ages can be affected, ranging from newborn babies to the elderly.

SUMMARY

For purposes of summarizing the disclosure, certain aspects, advantages and novel features have been described herein. It is to be understood that not necessarily all such advantages can be achieved in accordance with any particular embodiment disclosed herein. Thus, the embodiments disclosed herein can be embodied or carried out in a manner that achieves or optimizes one advantage or group of advantages as taught or suggested herein without necessarily achieving others.

In certain embodiments, a system for locating a patient-swallowed pill transmitter can include a pill transmitter. The pill transmitter can further include a circuit board. In some embodiments, the pill transmitter can include a first transmitting element electrically coupled with the circuit board. The first transmitting element can transmit a first signal, where the first transmitting element having a first axis substantially perpendicular to a longitudinal axis of the pill transmitter. The pill transmitter can further include a second transmitting element electrically coupled with the circuit board. The second transmitting element can transmit a second signal, where the second transmitting element has a second axis substantially perpendicular to the longitudinal axis of the pill transmitter and substantially perpendicular to the first axis of the first transmitting element. In some embodiments, the pill transmitter can include a third transmitting element electrically connected to the circuit board. The third transmitting element can transmit a third signal, where the third transmitting element having a third axis substantially parallel to the longitudinal axis of the pill transmitter.

The system of the preceding paragraph can have any sub-combination of the following features: wherein a longitudinal axis of the circuit board is substantially parallel to the longitudinal axis of the pill; wherein said third transmitting element is positioned on a side opposite from said first transmitting element with respect to the circuit board; wherein said third transmitting element is positioned on a first surface of the circuit board opposite from a second surface of the circuit board, second surface including said first and second transmitting elements; wherein said third transmitting element is positioned on a side opposite from said second transmitting element with respect to the circuit board; further comprising a plurality of circuit elements positioned on the circuit board such that the plurality of circuit elements do not intersect with at least one of the first axis or the second axis; wherein the circuit elements are positioned on a surface of the circuit board opposite from a surface of the circuit board electrically coupling said first and second transmitting element; a battery, wherein an axis of the battery is substantially perpendicular to the circuit board; wherein the battery does not intersect with at least one of the first axis or the second axis; further comprising a plurality of receivers configured to receive transmitted signals from at least one of the first, second, or third transmitting elements; wherein the plurality of receivers comprise a flat coil; further comprising a patient monitor configured to calculate a position of the pill based on the received signals; further comprising a timing module configured to set a time period for operation of said first, second, and third transmitting elements; and further comprising a control module configured to select an operating frequency for each of the first, second, and third transmitting elements.

Moreover, in some embodiments, a system for locating a patient-swallowed pill transmitter can include a pill. The pill can include a first transmitting element that can transmit a first signal at a first frequency in a first axis. The pill can further include a second transmitting element that can transmit a second signal at a second frequency different from the first frequency in a second axis substantially perpendicular to the first axis. In some embodiments, the pill can include a third transmitting element that can transmit a third signal at a third frequency different from said first and second frequency in a third axis substantially perpendicular to said first and said second axes.

The system of the preceding paragraph can have any sub-combination of the following features: further comprising a battery, wherein the battery does not intersect with at least one of the first axis or the second axis; further comprising a circuit configured to select said first, second, and third frequencies; a fourth transmitting element electrically coupled with the first transmitting element; a fifth transmitting element coupled with the second transmitting element; a sixth transmitting element coupled with the third transmitting element; further comprising a plurality of receivers configured to receive transmitted signals from at least one of the first, second, or third transmitting elements; and further comprising a patient monitor configured to calculate a position of the pill based on the received signals.

BRIEF DESCRIPTION OF THE DRAWINGS

Throughout the drawings, reference numbers are re-used to indicate correspondence between referenced elements. The drawings are provided to illustrate embodiments of the features described herein and not to limit the scope thereof.

FIGS. 9A-B illustrates an embodiment of a multiple transmitting elements per axis structure 900 using a notch design.

FIG. 10 illustrates an embodiment a pill 1000 including wire coils 1002, 1004, and 1006 wrapped around the inner circumference of the pill coating.

DETAILED DESCRIPTION

Figure 1A:
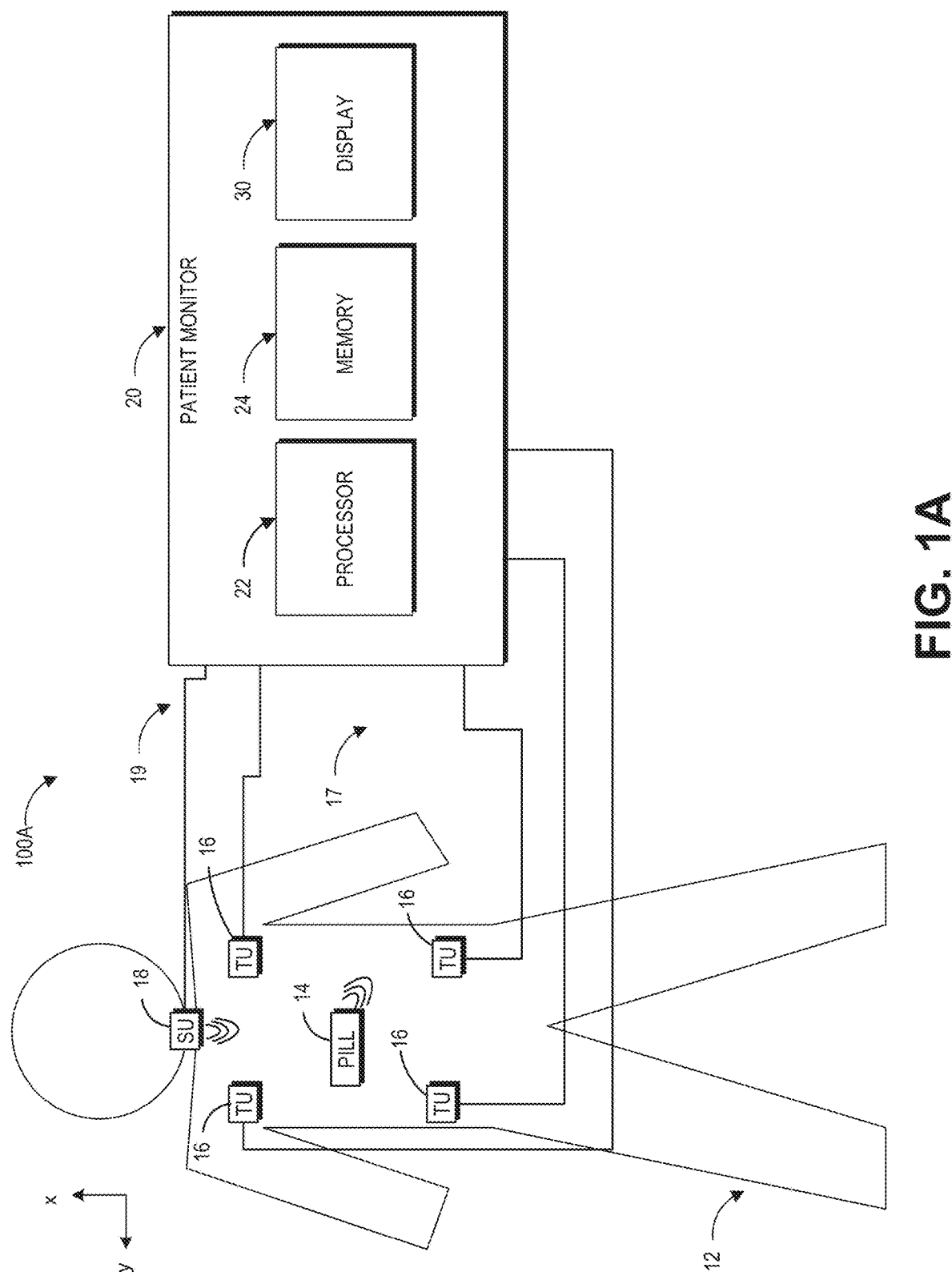
FIGS. 1A-B are block diagrams illustrating transmitter monitoring systems in accordance with embodiments of the disclosure.

Various embodiments will be described hereinafter with reference to the accompanying drawings. These embodiments are illustrated and described by example only, and are not intended to be limiting.

I. Introduction

For the past decade, the gastrointestinal ("GI") tract has become an area of intense scientific and public interest due to exciting discoveries of its importance in many aspects of human health and disease. However, understanding the pathophysiology of many gastrointestinal disorders is hampered by an inadequate ability to investigate primary GI functions with a technological means providing low patient stress, rapid and effective diagnostic data, and ease of use enabling universal adoption.

It would be beneficial to provide a highly effective, simple to implement, and inexpensive monitoring system to measure GI motility and general GI tract function. Certain embodiments of the systems described herein can provide some or all such benefits, overcome shortfalls of existing monitoring solutions, can be applicable to a variety of healthcare applications, and can be flexible and extendable to the treatment, research, and monitoring of many other GI diseases and conditions.

Embodiments of systems and methods described herein are designed to monitor the movement of one or more swallowed pill transducers through the human GI tract or digestive system, including the mouth, esophagus, stomach, large and small intestines, colon, and rectum, or any subpart thereof. These systems and methods can include hardware and/or software that can accurately track and record the movement of the pill or pills as they move through the GI tract to ultimate elimination. An external sensor system, which may include antennas, enables position tracking and/or flow rate of the pill(s) through the GI tract. The antennas can provide signals indicative of pill position to a processor, which can perform signal processing to determine pill location, flow rate, motility, or any of a variety of other measurements related to the pill(s). The processor can provide such measurements and information to a display (local to the processor or over a network, such as to a cellphone or personal digital assistant (PDA)) for presentation to a clinician, such as a physician, nurse, or other care personnel.

For example, in some embodiments, the systems and methods described herein use near field communications to locate a radiating transmitter, such as a pill swallowed by a patient. The system can be triggered to turn on and transmit an amplitude shift keyed waveform (or other type of waveform) to a set of antennas attached to, coupled with, or near the patient at roughly known locations. The magnetic field emitted by the transmitter can be measured by the receiving antennas, for example, using principles of mutual inductance. The receiving antennas may be tuned specifically to the frequency of the emitting transmitter for high sensitivity and high Q. The differential phase and/or time shifts between the antennas can contain sufficient information to find the location of the transmitter and optionally its orientation relative to body coordinates. Further, the amplitudes of received signals may also be used to calculate location and/or orientation of the pill. The system can display the location and/or orientation of the transmitter and may optionally provide other information about the movement, flow, or other characteristics of pill to assist clinicians with diagnosis.

In addition, in some embodiments, the pill may also include one or more additional sensors that output data, which the pill can transmit to the receiving antennas for processing by the processor. Examples of such sensors include pressure sensors, pH sensors, temperature sensors, camera(s), salinity sensors, and the like. In other embodiment, however, at least some of such sensors are omitted to reduce the size of the pill, thereby enabling the pill to be small and compact. With its small and compact shape, the pill can move in a similar manner to food particles and therefore more accurately represent digestive activity of a patient than current larger pill transmitters. Further, different size pill transmitters that act like different sizes of food particles can be swallowed by a patient and analyzed by the processor to provide a more comprehensive view of digestive activity for presentation to a clinician.

Thus, the systems and methods described herein can provide clinicians with the ability to identify obstructions, regurgitations, reflux, peristalsis, or other GI conditions that are dangerous to a patient's health and which are currently difficult if not impossible to monitor in a simple, low cost, real time, and non-invasive manner. Thus, the systems and methods described herein can facilitate diagnosing and/or treating numerous diseases and conditions, including, but not limited to, Crohn's disease, bowel strangulation, neuropathy, diverticulitis, paraplegia-related conditions, diabetic gastroparesis, functional dyspepsia, irritable bowel syndrome, epigastric pain syndrome, and post infectious and idiopathic gastroparesis. Further, the systems and methods described herein can facilitate treating patients with endocrine disorders such as hypo-/hyperthyroidism, pituitary and parathyroid disease, and Addison's disease.

Further, in some embodiments, the pill transmitter can include multiple transmitting elements for transmitting electromagnetic field towards the receiving antennas. Embodiments of the pill transmitter including multiple transmitting elements described herein can be used with the systems and methods described in application Ser. No. 13/969,435, incorporated herein by reference in its entirety, to calculate a location of the pill transmitter. Multiple transmitting elements can be beneficial in some embodiments for improving tracking of the pill as it moves through the GI tract.

II. Example Transmitter Monitoring System Overview

Prior to describing embodiments of pill transmitter including multiple transmitting elements in detail, an overview of example transmitter monitoring system is provided below with respect to FIGS. 1A through 2C. The transmitter monitoring system can include a transmitter (e.g. pill) and a plurality of antennas. The transmitter monitoring system can track location of the pill with respect to the plurality of antennas. In some embodiments, the transmitter monitoring system can also automatically track the positions of the plurality of receiver antennas.

For example, FIG. 1A shows an embodiment of a physiological monitoring system 100A. In the physiological monitoring system 100A, a medical patient 12 can ingest a pill 14, which can be tracked by a patient monitor 20. As discussed above, the pill 14 can include one or more transmitting elements (e.g. antennas) to transmit signals as it passes through the GI tract of the patient 12. In an embodiment, the pill 14 transmits a signal in response to a trigger signal from a stimulus antenna 18. The pill 14 may also be programmed to transmit signals at intervals without receiving a trigger signal. The stimulus antenna 18 can be positioned on the patient or with the patient monitor or in a room. The patient monitor 20 can control the operation of the stimulus antenna via a link 19. The plurality of transceiver units (TU) 16 can also include one or more antennas to receive the transmitted signals from the pill 14. In some embodiments, the plurality of transceiver units (TU) do not include any transmit functionality and may just include receiving antennas. In one embodiment, the system includes 5 TUs. In other embodiments, the system can include 10, 20, 50, or 100 TUs. Increasing the number of TUs can improve accuracy of measurements, but might require more processing.

The patient monitor 20 can collect the received signals from the plurality of receiving units 16 via a link 17 for processing by one or more processors 22. Links 17 and 19 can include wired or wireless (Bluetooth, NFC, WiFi or like) communication. The processor 22 can implement one or more modules for calculating the location of the pill 14 in the body of the medical patient 12. The location of the pill 14 can be tracked over time and stored in a memory 24 of the physiological monitor 20.

The processor 22 can communicate the processed signals or measurements to a display 30 if a display is provided. The display 30 can show real time position (in 2 or 3 dimensions) of the pill in the GI tract of the patient 12. In other embodiments, the position of the pill on the display may be updated periodically (e.g. every 1 second, 30 seconds, 1 minute, 5 minutes, 30 minutes, etc.). The update frequency of the display may be a function of the frequency of trigger or transmitted signals. In an embodiment, the display 30 is incorporated in the physiological monitor 20. In another embodiment, the display 30 is separate from the physiological monitor 20. For example, the physiological monitor 20 can transmit the processed signals over a network to the display 30. The physiological monitoring system 100 is a portable monitoring system in one configuration.

In some embodiments, the plurality of TUs 16 are removably attached at or near the body of the patient 12. In certain other embodiments, a frame (not shown) may structurally support the plurality of TUs 16. Accordingly, the patient 12 can be positioned within the frame structure. The TUs 16 may also be affixed on a bed frame. The strength of the transmitted signals from the pill 14 is inversely proportional with distance. Thus, in some embodiments, the TUs 16 are placed in close proximity to the body of the patient 12 or attached directly to the body or to object in close proximity of the patient 12. For example, the TUs 16 can be attached to bed sheets or mattresses. The TUs 16 can also be attached to the clothing of the patient, such as a vest or an undershirt. The TUs 16 may be attached, for example, with a suitable adhesive to the skin. In some embodiments, the TUs can be sewn or staples with the materials.

Figure 1B:
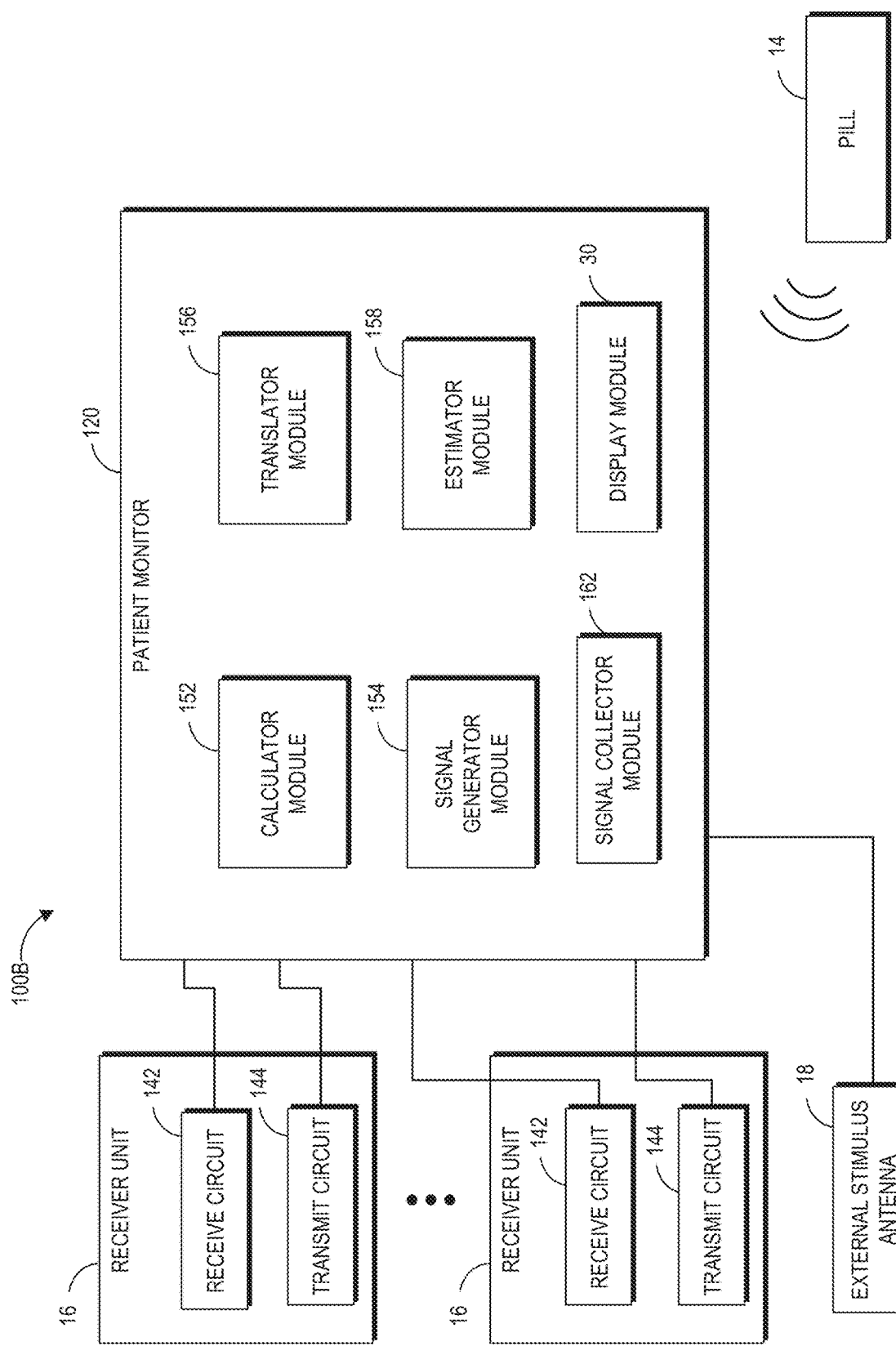

FIG. 1B illustrates a block diagram of an embodiment of the physiological monitoring system 100B. The transceiver units 16 include a receive circuit 142 for receiving signals from the pill 14. In some instances, the transceiver units 16 may further include a transmit circuit 144. The transmit circuit 144 and the receive circuit 142 may include an antenna. In some embodiments, the transmit and receive circuitries can share a common antenna. Further, the transmit circuit 144 and the receive circuit 142 may include multiple transmitting elements as described below with respect to the pill transmitter. In certain embodiments, having multiple transmitting elements may offer some of the advantages discussed herein with respect to the pill transmitter. For example, multiple antennas may provide a better line of sight in some embodiments for tracking the pill and/or tracking the receiver antennas.

In an embodiment, the pill 14 can also include transmit and/or receive circuitry as described more in detail below with respect to FIG. 2A. The pill can transmit a signal waveform in response to receiving a trigger signal from the stimulator antenna 18 or independently of such stimulus. The signal generator module 154 of the physiological monitor 20 can instruct the stimulator antenna 18 via the link 19 to transmit the trigger signals. In an embodiment, the signal generator module 154 can generate the trigger signal waveforms. The trigger signals may be generated over a predefined time interval (e.g. every 1 second, 30 seconds, 1 minute, 5 minutes, 30 minutes, etc.). The time interval may have a pattern or can be randomized. In some embodiments, users can control the generation of trigger signal via the physiological monitor 20. The trigger signals may also be generated depending on the location of the pill in the patient 12. For example, in a slow moving section of the GI tract, the frequency of triggers signals may be lower than in a fast moving section of the GI tract. In some embodiments, the pill may transmit the signal waveform without continuously requiring external trigger signal. For example, a first trigger signal may activate the pill 14 and thereafter the pill 14 may emit a waveform once every pre-determined time interval for a particular duration. The first trigger signal can be received wirelessly or via a switch. The pill may include a battery to generate transmit signals. For embodiments of the pill including multiple transmitting elements, the transmit circuit of the pill can sequentially activate the multiple transmitting elements.

The signal collector module 162 of the physiological monitor 20 can collect the signal waveforms, transmitted by the pill 14, from the transceiver units 16. The phases of the received signals at TUs 16 may vary according to the time it takes the transmitted waveform to travel from the pill to the TU 16. The travel time (or time of flight) is also a function of the distances between the pill and the TUs 16. As such, the phase shifts in the received signals at the first and the second TU may vary depending on the relative locations of the TUs 16. In some embodiments, the calculator module 152 of the physiological monitor 20 can obtain the phase and the amplitude shifts from each of the collected signals. The calculator module 152 can calculate the location of the pill 14 in the patient 12 by applying one or more rules, analysis, and/or filtering on the phase and/or amplitude shifts.

In some embodiments, the location of the pill 14 can be calculated from the phase differences between the received signals at one or more pairs of the TUs 16. For example, a first TU 16 can receive a transmitted signal from the pill 14. A second TU 16 can also receive the same transmitted signal from the pill 14. In certain embodiments, the calculator module 152 can calculate the location of the pill 14 in the patient 12 by applying one or more set of rules on the phase differences between the first and the second TUs. The calculator module 152 can also apply one or more of rules on a combination of measured parameters—phases, amplitudes, and phase differences—to calculate the location of the pill 14. In some embodiments, the measured parameters can be obtained from application of signal processing techniques on the received signals. Moreover, for a pill including multiple transmitting elements transmitting signals respectively, the calculator module 152 can use the received signal with the largest interaction for calculating the location of the pill.

The rules can include linear, non-linear, or a combination of linear and non-linear set of operations. In some embodiments, an estimator module 158 may use one or more linear operations to calculate an estimate for the location of the pill 14. The calculator module 152 may then use the estimate in one or more non-linear operations to calculate a more accurate location for the pill 14. In certain embodiments, a calibration process, described more in detail below, can improve the calculation for pill location by calibrating one or more system parameters, such as pill design, TU design, location of the TUs, and the orientation of the TUs. Calibration may be performed with a training data set. In certain embodiments, the physiological monitoring system 100 can adaptively calibrate the system parameters while tracking the pill 14 through the GI tract of the patient. Adaptive calibration can include automatically tracking the location and/or orientation of the TUs 16. As described above, TUs may be attached to a patient. Accordingly, the positions and orientations of the TUs 16 may change with patient movement and the shift in TU positions may affect the quality of pill tracking. Adaptive calibration can be made an instant before the TU locations are used to find the location of the pill.

Automatically monitoring the positions of plurality of TUs 16 can increase the accuracy of pill tracking. As described above, TUs 16 may also include a transmitter circuit 144 for transmission of a signal waveform. The signal generator module 154 can generate a plurality of transmit signals for transmission in a first order from the plurality of TUs 16. In an embodiment, the signals are transmitted one at a time from the plurality of TUs 16. For example, a first TU 16 may transmit a first transmit waveform. The plurality of non-transmitting TUs can receive the first transmitted waveform, which can be collected by the signal collector module 162. Subsequently, a second TU 16 may transmit a second transmit waveform. In some embodiments, the first and the second transmit waveforms are substantially similar. Again, the plurality of non-transmitting TUs 16 can receive the second transmit waveform, which can also be collected by the signal collector 162. The process can continue for each of the plurality of TUs 16. In certain embodiments, a subset of the plurality of TUs 16 may be used to transmit signals. The signal collector module 162 can collect, for each transmitted signal, signals received at plurality of the non-transmitting antennas via links 17. The calculator module 152 can apply one or more rules, analysis, and/or filtering on the collected signals to calculate the location of the plurality of TUs as described in detail in application Ser. No. 13/969,435. In some embodiments, the rules can include a modified set of operations from a multilateration analysis.

III. Example Pill Transmitter Embodiment

Figure 2B:
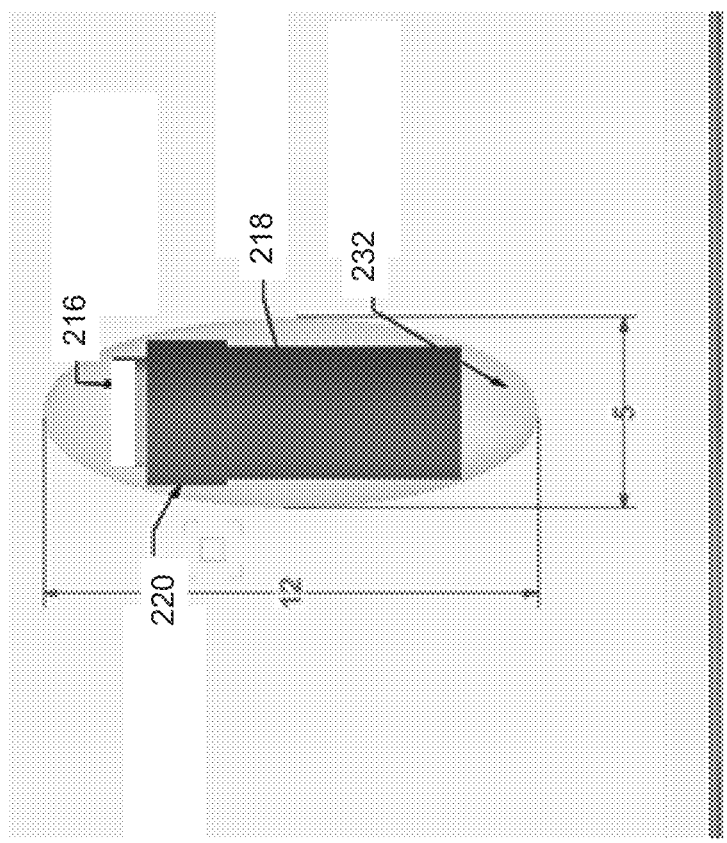
FIG. 2B illustrates a cross section view of a pill transmitter in accordance with an embodiment of the disclosure.
Figure 2A:
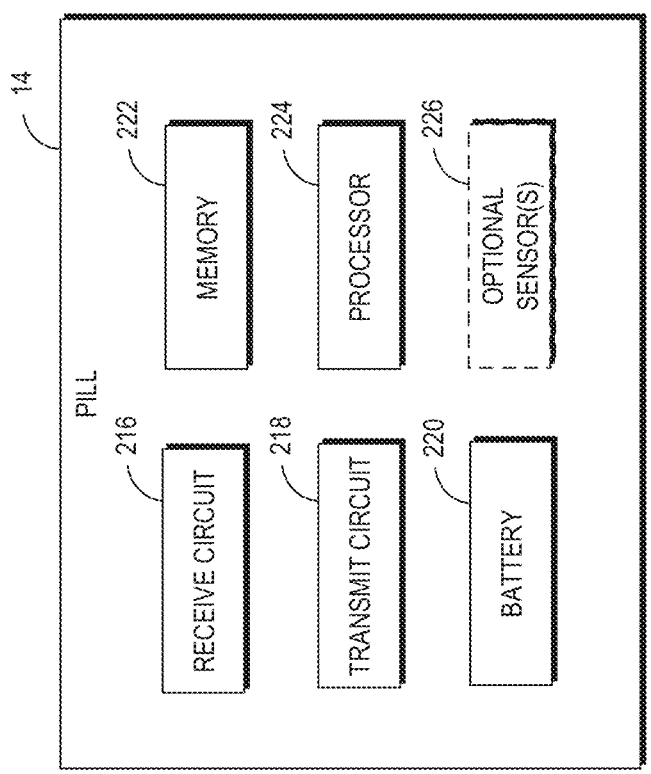
FIG. 2A is a block diagram illustrating a transmitter pill in accordance with an embodiment of the disclosure.

FIG. 2A illustrates an example block diagram of an embodiment of a pill 14 that can be ingested by a patient. The pill 14 can include a transmitter circuit 218 including an antenna for transmitting a signal waveform. In some embodiments, the pill 14 includes multiple transmitting elements or antennas as described in detail below. While described herein as a transmitter, the pill may be a transponder or transceiver including receive functionality in some embodiments. In some embodiments, the pill 14 can transmit a signal waveform in response to an external trigger signal. The receive circuit 216 in the pill 14 can also include an antenna to receive the trigger signal from the external stimulator antenna. The receive circuit 216 and the transmit circuit 218 may share an antenna. The antenna may be referred to or be configured as a loop antenna. The antenna may also be referred to or be configured as "magnetic antenna" or an induction coil. The antenna may also include a coil of a type that can wirelessly output or receive wireless communication signals. In some embodiments, the antennas may also wirelessly output or receive power. The pill can also include commercially available or custom RFID tag. In some embodiments, the pill can operate in a passive mode of operation. In the passive mode of operation, the pill may not require a battery or power storage device 220. The external trigger signal can provide sufficient power to the pill for transmitting the signal waveform. The pill may also operate in an active mode or battery-assisted passive mode, requiring an on-board battery or a power storage device 220. In the battery-assisted passive mode, the on-board battery 220 can be smaller than in the active mode.

In the active mode, the pill 14 can periodically transmit the waveform signal. The pill 14 may transmit the signals based on a predetermined time intervals and at predetermined transmission frequencies. For example, after receiving an external stimulus (before or after ingesting the pill), the pill can transmit a signal waveform over a time interval (e.g. every 1 second, 30 seconds, 1 minute, 5 minutes, 30 minutes, etc.). The pill may also transmit the signal waveform continuously but that may increase the power duty cycle. In some embodiments, the external signal can be a mechanical switch. The switch may be turned on before ingesting the pill causing it to periodically transmit a signal waveform. The on-board battery may provide sufficient power for the pill to transmit the signals over a span of several days.

In the passive or battery-assisted passive mode, the pill 14 can transmit a signal waveform in response to receiving the trigger signal. The circuitry in the pill can activate in response to the trigger signal and transmit a signal waveform. The pill 14 can then go into a passive state until the next trigger signal is received. In certain embodiments, the physiological monitor 20 can control the generation of trigger signals and transmission from the external stimulus antenna. The trigger signals may be generated over a time interval, for instance, every 1 second, 30 seconds, 1 minute, 5 minutes, 30 minutes, etc.

The waveform characteristics of the transmit signal can be stored in a memory 222 of the pill 14. The waveform characteristics can also be defined by the circuit elements of the transmit circuitry 218. In some embodiments, the transmit waveform can correspond to the characteristics of the trigger signal. The transmit waveform can also be modulated to reduce interference from external signals. Some of the modulation techniques can include Amplitude Shift Keying, Phase Shift Keying, or Frequency Shift Keying. In an embodiment, the duration of the transmit waveform is 1 ms. In other embodiments, the duration of the transmit waveform can be 0.1 ms, 10 ms, 100 ms. The pill may also the transmit the signal continuously.

The frequency characteristics of the transmit waveform can depend on several parameters. For example, at higher frequencies of more than 20 MHz, absorption of the signal waveform by the body tissue and organs may become significant. Furthermore, far field circuit antennas, may require precisely tuned GHz circuitry resulting in complex and expensive system. Near field coupling can allow for simpler electronics and communication via lower frequencies in the range of MHz. In an embodiment, the frequency of the transmit waveform is approximately 13.56 MHz which is part of the industry, scientific, and medical (ISM) radio band. At this frequency, there may be some absorption, but the transmit waveform can pass through 10 cm or more of body tissue. In another embodiment, the frequency of the transmit waveform is approximately 125 KHz. In yet another embodiment, the frequency of the transmit waveform is 6.8 MHz. At lower frequencies, the absorption from the body may be significantly reduced. In other embodiments, any frequency below 20 MHz may be used to reduce absorption. Frequencies equal to or higher than 20 MHz may also be used in certain embodiments. The frequency may also depend on the power constraints of the emitted waveform. For example, there are limits on power emissions of signals defined by industry standards and regulatory agencies to protect human body. Accordingly, in one embodiment, the power of the transmitted waveform is on the order of microwatts, or milliwatts, or 3 watts or less, or some other value.

In some embodiments, for pills including multiple transmitting elements, at each cycle, the pill can transmit from each of the multiple transmitting elements. In some embodiments, the transmission from multiple transmitting elements does not overlap in time. Further, the multiple transmitting elements of the pill can be arranged such that transmission from one of the multiple transmitting elements does not interfere with other transmitting elements of the pill. The arrangement of the transmitting elements and mode of operation is discussed more in detailed below.

FIG. 2B illustrates a cross-section 250 of an embodiment of a pill transmitter 14. The electronics in the pill can be encapsulated with a material 232 that is suitable for ingestion, for example, polytetrafluoroethylene (PTFE). The size of the pill 14 can vary depending on the size of the circuitry, for example, the size of the battery 220. In an embodiment, the size of the pill 14 is 5 mm×12 mm. For a pill with a smaller battery, the size can be reduced to 4 mm×6 mm capsule. The pill 14 can include one or more transmitting elements or antennas. In some embodiments, for a pill including multiple antennas 218, the antennas are arranged to maximize available space for the battery 220. The pill 14 may also include receive circuit 216. Further, the antennas may be arranged in the pill to minimize interference with the metal in the battery. That is, in some embodiments, at least some of the antennas transmit in an axis not intersecting the body or volume of the battery. In an embodiment, the antenna includes a ferrite core and may have a micro rod design to improve its signal transmission performance.

One benefit of the shape and size of the pill in certain embodiments is that the pill can be small enough that it acts like food. Thus, the pill can move with food and therefore mimic the motility or GI problems that food is having in the patient's body. The size of the pill is small in certain embodiments because the pill may not have a bulky camera or other sensors as in other existing pill designs. Existing pills from other manufacturers can actually be so large that they become obstructions themselves. In contrast, in certain embodiments, the pill described herein can be about 6 mm in length or less. Alternatively, the pill may be about 1.2 cm in length or less, or a slightly greater size. The smaller size pill can move with smaller sized bits of food, while the larger sized pill can move with larger bits of food. Different sized pills can therefore be used to diagnose or analyze different illnesses. In fact, different sized pills (including more than 2 different sizes) can be swallowed by the patient and tracked at the same time to track both small food movements and larger food movements. Any number of pills may be swallowed and tracked at one time, for example, up to 5 pills, or up to 10 pills, or up to 24 pills, or up to 48 pills. In one embodiment, detecting solely motility can be accomplished using a single pill, but also detecting obstructions can be accomplished using multiple pills.

IV. Magnetic Field

As discussed above, the pill transmitter can include one or more transmitting elements or antennas for transmitting at least magnetic or electromagnetic field towards one or more receiving antennas. In some embodiments, the transmitting element can create a magnetic dipole. For example, in some embodiments, the transmitting element is a wire coil wrapped around a core. A transmit circuit can generate a time-varying electrical current to run through the wire coil transmitting element so as to generate a magnetic field about the wire coil transmitting element. The core of the transmitting element can be ferromagnetic or non-magnetic. In some embodiments, ferromagnetic cores may amplify the dipole magnetic field produced by the current flowing through the coil. Magnetic cores can include materials such as ferrite or any other suitable magnetic material.

Figure 2C:
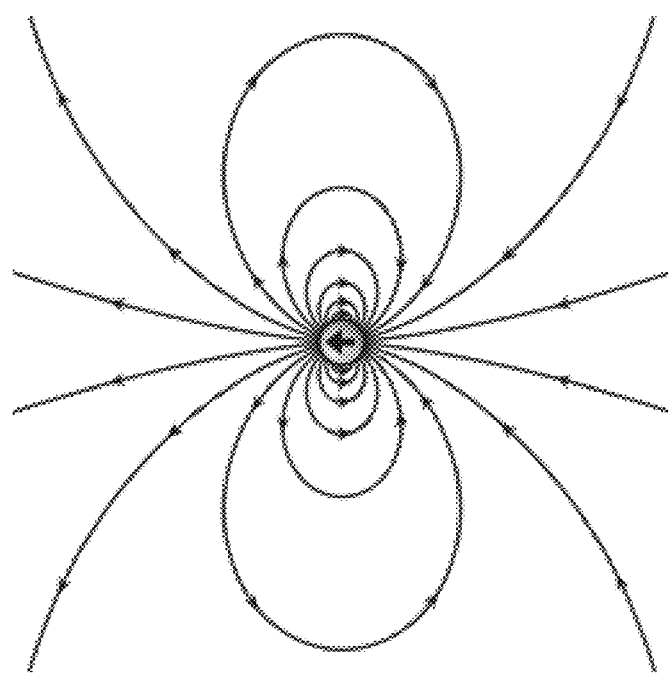
FIG. 2C illustrates an example magnetic dipole field emanating from a single current loop transmitting element.

As discussed above, the location of the pill transmitter can be calculated based in part on the interaction of the generated magnetic field from the transmitting element in the pill transmitter with the receiver antennas. The coupling of the transmitted field with a receive antenna can depend on the component of the transmitted dipole field that presents the greatest flux to the receiver antenna. For frequencies below 100 MHz, the radial component $B_r$ of the transmitted field may strongly couple with a planar coil arranged to receive a flux directed outward from the dipole. Magnetic dipole fields can be highly directional. FIG. 2C illustrates an example magnetic dipole field of a single current loop transmitting element. As shown, the radial component of the field can be maximum parallel to the z-axis (direction of arrow in the illustrated example) and zero on the equatorial plane (x-y plane). At an angle θ off the z-axis, the magnitude of the example field is proportional to cos θ. Accordingly, a receiving antenna located on the x-y plane or generally off from the z-axis may see little to no magnetic field from the pill transmitter. The spherical radius r and polar θ field components of a single dipole of moment m, relative to its axis (the z axis in this equation) can be calculated as follows:

$$B_r = \hat{r} \cdot B = \frac{\mu_o}{4\pi} \frac{2\hat{r} \cdot m}{r^3} = \frac{\mu_o}{4\pi} 2\cos\theta \frac{m}{r^3} \quad (1)$$

$$B_\theta = \hat{\theta} \cdot B = \frac{\mu_o}{4\pi} \frac{3(\hat{r} \cdot m)(\hat{\theta} \cdot \hat{r}) - \hat{\theta} \cdot m}{r^3} = +\frac{\mu_o}{4\pi} \sin\theta \frac{m}{r^3}$$

Since $B_r$ is proportional to cos θ, its value remains larger than half its maximum value out to θ=60 degrees off-axis.

Further, in some embodiments, the receiver antennas are flat and may include a planar receiving coil. The flat antennas may be affixed to the body of the patient. As the pill passes through the digestive system of a human body, it may be in any unknown orientation. Accordingly, the transmitting element in the pill may also be in any random orientation. Once the pill is inside the body, its orientation may not be generally controlled. Thus, there may be time periods when the receiver antennas on the patient's body pick up little to no transmitted field from the pill's transmitting elements. Accordingly, it may be beneficial in some embodiments to generate a nearly isotropic or isotropic time-averaged field compared to that illustrated in FIG. 2C.

V. Pills with Multiple Transmitting Elements

Figure 3:
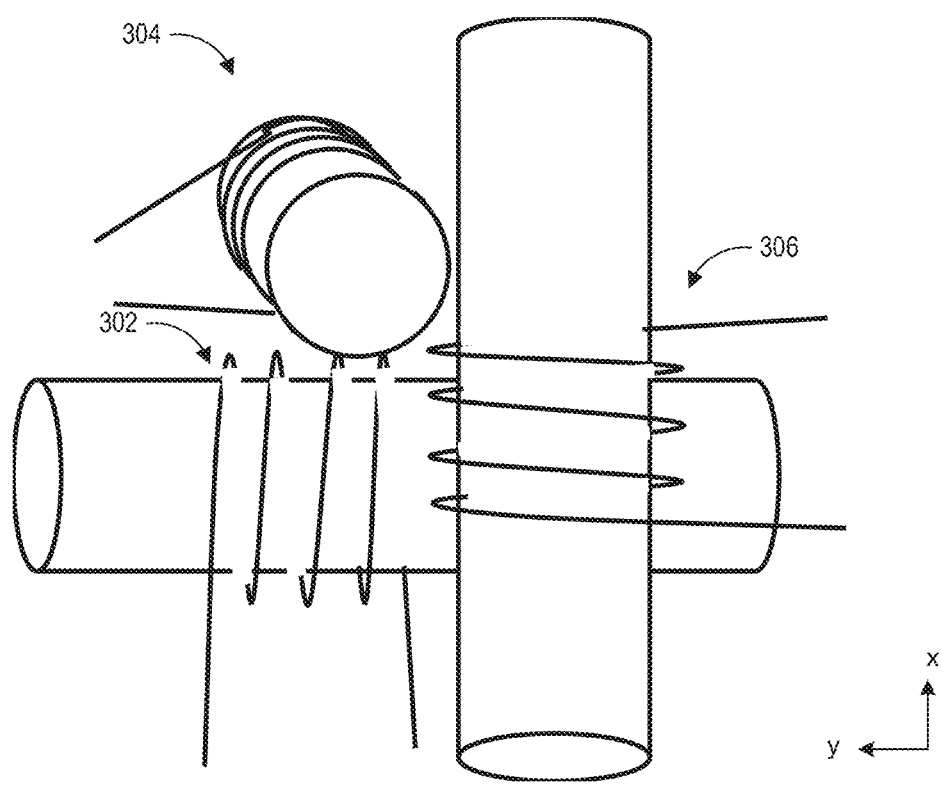
FIG. 3 illustrates an example arrangement of multiple transmitting elements for generating a nearly isotropic time-average field.

FIG. 3 illustrates an example arrangement of multiple transmitting elements that can generate a nearly isotropic time-average field. In the illustrated example, each of the transmitting elements include a wire coil for generating magnetic field when an electric current is passed through the coil. For instance, coil 302 is oriented to transmit a magnetic field parallel or substantially parallel to the z-axis. In the depicted embodiment, coils 304 and 306 are oriented to transmit a magnetic field parallel or substantially parallel to the x and y axis, respectively. The coils may include a ferrite core. The coils 302, 304, and 306 can be co-located within a pill. Two or more of the coils 302, 304, 306 may be physically separated from each other within the pill by a gap or a distance. The separation distance may be 1 mm or less, or 5 mm or less, 10 mm or less. Further, in the illustrated arrangement, the three coils are positioned orthogonally with respect to each other. In some embodiments, the three orthogonally-arranged coils can generate a magnetic field pattern that is more likely to reach a receiving antenna located proximate to the body of a patient compared to a single transmitting element. As discussed above, a single transmitting element may transmit in substantially one direction that is not in the path of receiving antennas. Furthermore, orthogonal arrangement of transmitting elements can reduce cross-coupling or near-field coupling. In some embodiments, the pill may include only two orthogonal transmitting elements. The pill may also include more than three orthogonal transmitting elements. For example, each orthogonal axis may include more than one transmitting elements. In some embodiments, a transmitting element may also have an axis that is parallel to direction of transmitted magnetic field from the transmitting element. For a transmitting element including a loop or a coil antenna, the axis of the transmitting element may be perpendicular to the loop or coil.

The processing electronics and circuitry discussed above can control operation of each of the three coils independently. For example, the transmit circuitry can vary the timing, current magnitudes, frequency, or the phase of the three coils independently. Thus, in some embodiments, the transmit circuit can control the direction of transmission of the magnetic field by varying the parameters at individual coils. While the illustration only shows three transmitting elements, the pill can include more than three transmitting elements. For example, the pill can include 2, 4, 6 or more transmitting elements. However, in some embodiments, increasing the number of transmitting elements may increase crosstalk interferences.

As the currents in each loop shown in FIG. 3 are varied, the direction of the resulting dipole can be proportional to:

$$m \propto I_x(t)\hat{x} + I_y(t)\hat{y} + I_z(t)\hat{z} \quad (2)$$

where $I_x(t)$ is the current in the x-directed coil, and $I_y(t)$, and $I_z(t)$ are the currents in, respectively, the y- and z-directed coils. By varying the timing, magnitudes, and phases of the currents, the direction of the maximum field in any desired direction can be controlled as a function of time. As the peak lobe has an angular breadth, any direction can be exposed to a desired fraction of the maximum field for any desired time. For example, in one embodiment, the radial field component exceeds ¾ maximum out to 41° off axis from the dipole direction. Further operating details of the pill including multiple transmitting elements is discussed more in detail below after the discussion of various embodiments of pill including multiple transmitting coils.

VI. Example Pill with Orthogonal Transmitting Elements

Figure 4A:
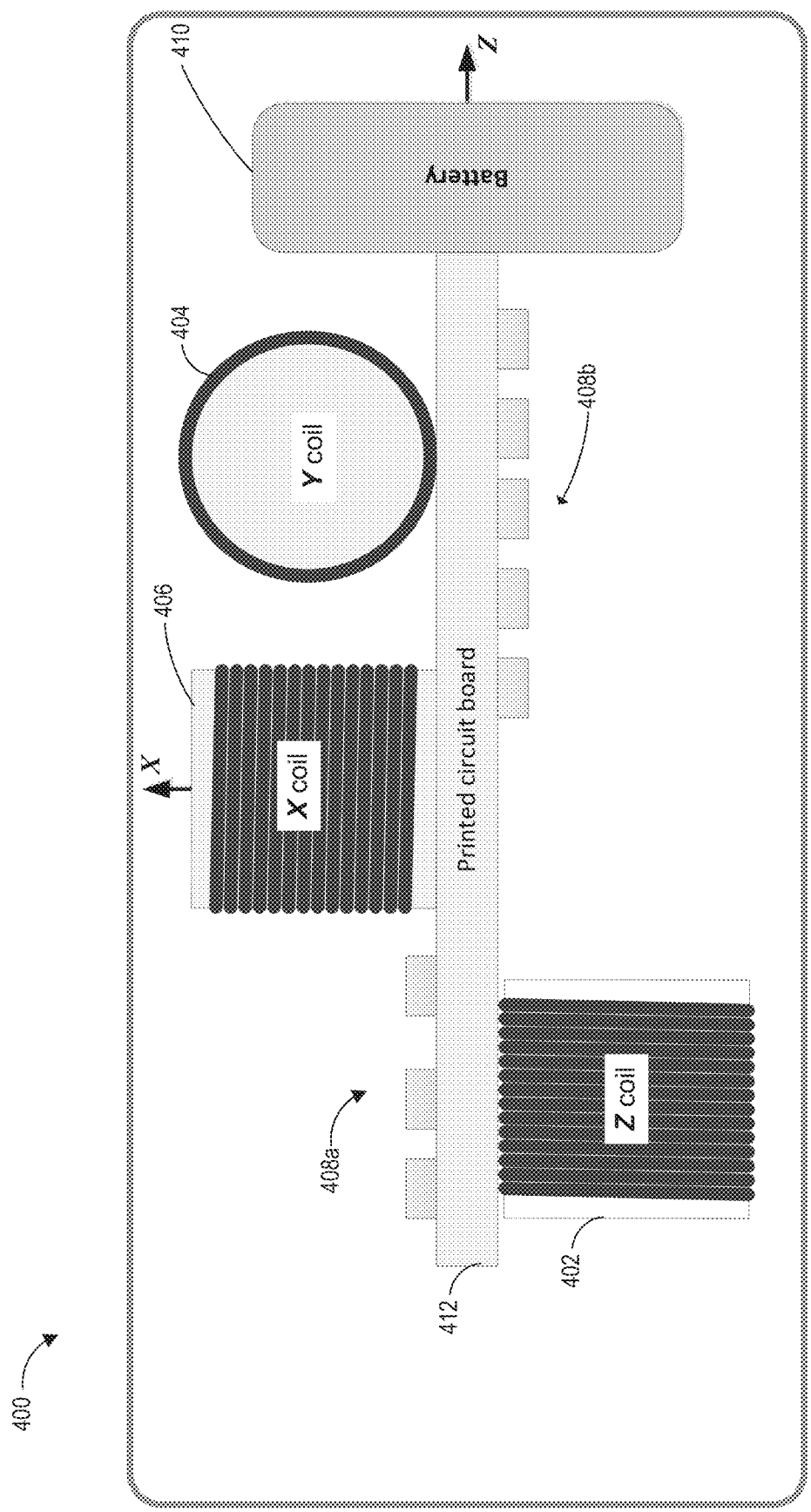
FIGS. 4A and 4B illustrate a front view and an end view respectively of an embodiment of a pill 400 including multiple transmitting elements.
Figure 4B:
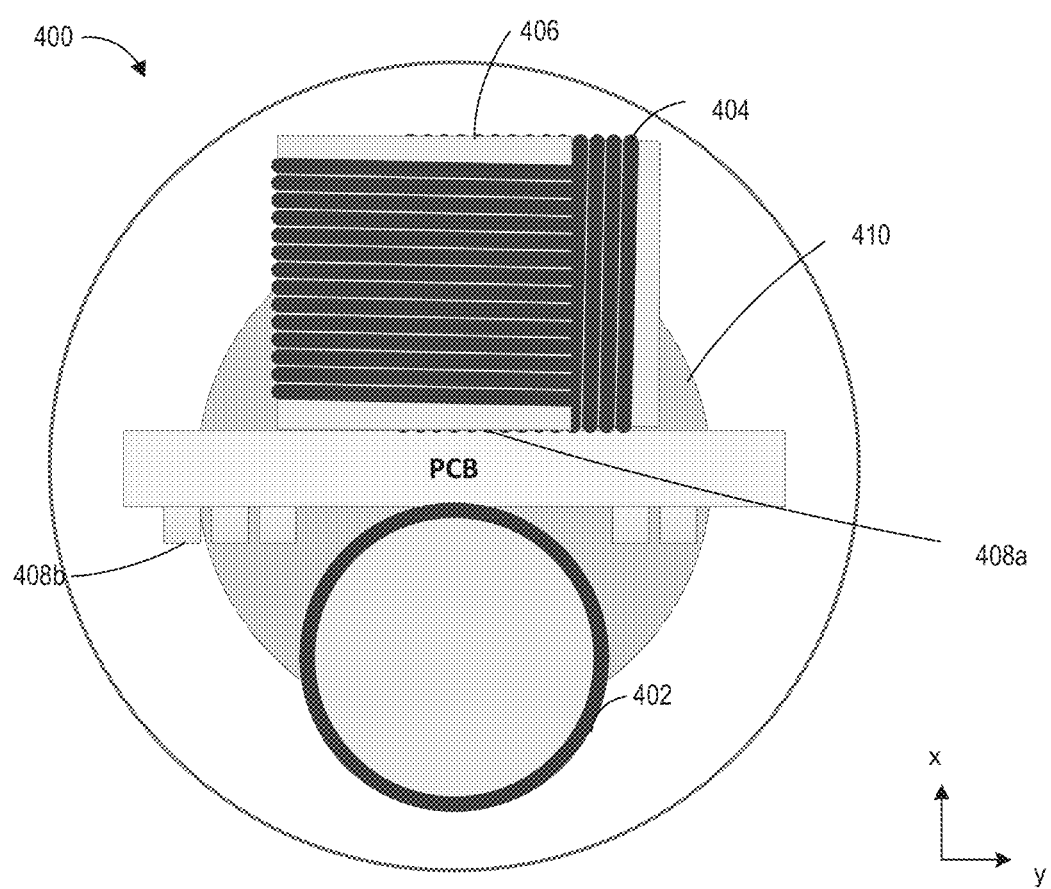

FIGS. 4A and 4B illustrate a front view and an end view respectively of an embodiment of a pill 400 including multiple transmitting elements. In the illustrated embodiment of FIG. 4A, the longitudinal axis of the pill 400 is parallel to the z-axis shown. In some embodiments, the pill 400 is substantially rectangular or ellipsoidal in shape. As discussed above, the size of pill may be constrained by whether a patient can comfortably swallow the pill. Further, the orientation of the pill as it traverses the GI tract may also depend on the shape of the pill. The orientation of the swallowed pill may vary over time in the GI tract. However, in some embodiments, the pill may be oriented along some axes more often (majority orientation) than other axes (minority orientation) over time as it passes through the GI tract. For example, the longitudinal axis of the pill may be oriented parallel to the longitudinal axis of the patient or the transverse axis of the patient for a longer time period compared to the frontal axis of the patient's body during the pill's passage in the GI tract. The longitudinal axis of the patient 12 can run from head to toe of a patient 12 and is parallel to the x-axis shown in FIG. 1A. Further, the transverse axis of the patient 12 may cut across the body of a patient dividing it into a front half and a back half and may be parallel to the y-axis shown in FIG. 1A. The frontal axis of the patient 12 may be perpendicular to both the x and y axes of FIG. 1A, bisecting the body of the patient in a left half and a right half. Thus, in some embodiments, the majority of the volume of the pill is more likely to be in a plane parallel to the frontal plane (x-y plane of FIG. 1A) of the patient's body as it traverses the GI tract.

The transmitting elements of the pill can be arranged to take into account the orientation of the pill that occurs a majority of the time. For example, in the illustrated embodiment of pill 400, the transmitting elements 404 and 406 are positioned to emit magnetic fields in a direction substantially perpendicular to the longitudinal axis of the pill and accordingly may be primary sources of magnetic field emission that is received by the antennas on the patient's body. As a result, the receiving antennas may experience stronger signal from at least two antennas, improving the probability of receiving a signal from the pill as it traverses through the GI tract. Accordingly, the location calculation can be more accurate because of improvement in signal to noise ratio (SNR).

In some embodiments, the size of the battery 410 may also impose a design constraint. Generally, the capacity of a battery is proportional to its size (e.g. surface area). Thus, larger capacities batteries may require more volume. However, the size of the pill may be limited based on a patient's swallowing comfort. Furthermore, most batteries include metallic components (e.g. electrodes) that may interfere with the transmitted field from one or more of the transmitting elements. Accordingly, in some embodiments, it may be beneficial to orient the battery 410 relative to the transmitting elements 402, 404, and 406 in the pill to improve one or more operational specifications: maximizing available battery space, reducing interference with the transmitted field; and/or increasing transmitted field in the majority orientation.

In the illustrated embodiment of FIG. 4A, the battery 410 is positioned to occupy a portion of the pill with little to no interaction from at least two transmitting elements of the pill 400. As shown, in some embodiments, the battery 410 included in the pill 400 is positioned such that the surface area vector of the battery 410 is substantially parallel to the longitudinal axis of the pill 400. The surface area vector can be parallel to a normal line to a plane defined by a rear surface of the battery. In some embodiments, the surface area vector of the battery 410 is perpendicular to the largest surface area of the battery 410. A transverse axis of the battery can be substantially parallel to the largest surface area of the battery. For the illustrated embodiment shown in FIG. 4A, the surface area vector is parallel to the z-axis.

Further, in the illustrated embodiment, the transmitting elements 406 and 408 are positioned to transmit the magnetic field away from the battery 410. For example, the transmitting element 406 can include a wire coil that when time-varying current is applied can transmit the magnetic field in a direction substantially parallel to the x-axis. Similarly, the transmitting element 404 can also include a wire coil that when time-varying current is applied can transmit magnetic field in a direction substantially parallel to the y-axis. The axis of the wire coil or loop transmitters described herein can be referred to as a direction perpendicular to the surface area of the loop. In the illustrated embodiment of FIG. 4A, the y-axis is coming out of the page. Accordingly, the majority of the magnetic field from transmitting elements 406 and 408 may leave the pill 400 towards the receiver antennas with little or no interference from the battery. The transmitting element 402 may be positioned to transmit field in a direction substantially orthogonal to both the transmitted field from transmitting elements 404 and 406. Thus, in the illustrated embodiment, the transmitting element 402 is positioned to transmit most or all of its radiative energy parallel to the z-axis. The transmitting element 402 may generate field towards the battery 410. Accordingly, there may be some interaction of the transmitted field from the element 402 with the battery 410. Thus, in some embodiments, the transmitting element 402 is positioned at a distance away from the battery 410 to reduce interference from the battery 410. Positioning the transmitting element 402 farther away from the battery may increase the angle of field leaving the pill 400.

Further, the pill 400 may include circuit elements 408a and 408b. The circuit elements 408 may drive the transmitting elements of the pill. In some embodiments, however, the circuit elements 408 may also interfere with the transmitted field from the transmitting elements. The circuit board 412 might have space constraints for mounting circuit elements 408. For example, in some embodiments, the circuit board 412 may mechanically support the transmitting elements 402, 404, and 406, resulting in reduced available space for mounting circuit elements. In additional embodiments, the transmitting elements 402, 404, and 406 may be electrically connected to the circuit board 412 via conductors or a daughter board, for example, and may not be connected directly to the circuit board 412.

Also, there may be some portions or pockets on the circuit board 412 that are substantially not in the path of the transmitted field emitted from one or more of the transmitting elements 402, 404, and 406. For example, there may be portions of the circuit board 412 that do not overlap with the transmitting elements 402, 404, and 406. Moreover, the portions may be on opposite surfaces of the circuit from the surface with one or more transmitting elements. The portion may also be on an end of the circuit board that is farther from one or more transmitting elements. Further, in some embodiments, the circuit board 412 may also be flexible.

In the illustrated embodiment of the pill 400 in FIG. 4A, at least some of the circuit elements 408a are mounted on a portion of the circuit board 412 that may distort little to no transmitted field energy in view of the orientations of transmitting elements 402, 404, and 406. For example, since at least some of the circuit elements 408a are placed on a surface of the circuit board 412 opposite the Z coil 402, which has an axis and hence main field direction perpendicular to the board 412, fields from the circuit elements 408a may have little or no interference on fields from the Z coil 402. For similar reasons, additional circuit elements 408b are placed on the board 412 and may have little or no interference on the fields generated by the Y coil 404. Since few or no circuit elements 408b are opposite the X coil 406, even though the X coil's 406 fields may flow through the board 412, the circuit elements 408b may also not interfere substantially with the X coil's 406 fields. However, the circuit elements 408b may interfere at least partially with the transmitted field energy from the transmitting element 402 due to being aligned with the fields generated by the Z coil 402. Thus, the additional circuit elements 408b are shown mounted at a distance away from transmitting coil 402 to reduce the amount of interference of the elements 408b on the coil 402. In some embodiments, not shown, none of the additional circuit elements 408b overlap with the portion of the circuit board 412 on which the transmitting coil 406 is affixed. Since an axis of the X coil 406 extends through the circuit board 412, to reduce interference from the circuit board itself on the X coil 406, the thickness of the circuit board 412 and location of conductive circuit traces and ground planes in the board 412 may be selected so as to reduce any interference with the magnetic field emitting from the transmitting coil 406. For example, the circuit traces and/or grounds planes under the X coil 406 may be reduced in thickness relative to traces and/or ground plane in other areas of the board 412, or may be routed around the X coil 406 in part or entirely so that very little, if any, metal is on the board 412 under the X coil 406.

Moreover, the transmitted field from a transmitting element of the pill may interfere or couple with one of the other transmitting elements of the pill. Accordingly, in the illustrated embodiment of the pill 400, two of the transmitting elements 404 and 406 are positioned on a top portion of the pill above a y-z plane and a third transmitting element 402 is positioned on a bottom portion of the pill below a y-z plane. In some embodiments, the circuit board 412 is substantially parallel to the y-z plane. For example, the longitudinal axis of the circuit board 412 can be substantially parallel to the longitudinal axis (z-axis) of the pill. Accordingly, one of the transmitting elements can be mechanically and electrically attached on the bottom side of the circuit board 412, while the other two transmitting elements can be mechanically and electrically attached to the top side of the circuit board 412 as shown in FIG. 4A. In some embodiments, one or more of the transmitting elements 402, 404, and 406 may be mechanically attached to the pill outer casing.

Additionally, in some embodiments, each of the transmitting elements 402, 404, and 406 are positioned to transmit much or a majority of its magnetic fields in a direction that is orthogonal or substantially orthogonal to the other transmitting elements. In FIG. 4A, the transmitting elements 402, 404, and 406 include wire coil antennas. As discussed above, other types of antennas can also be used for generating magnetic fields. The circuit elements 408 may generate time-varying currents to pass through the wire coil antennas for generating magnetic field, which may be directional as discussed above. Accordingly, orienting the transmitting elements orthogonally with respect to each other can, in some embodiments, can reduce or prevent cross-talk or cross-coupling. Due to manufacturing inconsistencies, there might be some variation in the positions of the transmitting elements. For instance, the transmitting elements may be separated by approximately 90 degrees within a margin. The margin can be less than one degree. The margin can be also be 1 to 10 degrees. In some embodiments, the margin can be more than 10 degrees. In one embodiment, the size of the pill 400 is 9 mm by 20 mm, although smaller sizes (such as 5-7 mm in one dimension) or slightly larger versions are also possible.

FIG. 4B illustrates an end view of the embodiment of the pill 400 shown in FIG. 4A. As illustrated, the circuit element 408b can be positioned as to not interfere with the transmitted field. Further, in some embodiments, the transmitting element 404 may be offset with respect to transmitting element 406 as shown. The offset may decrease cross-talk or coupling between the two transmitting elements.

VII. Three Axis Helmholtz Coil Structure

Figure 5:
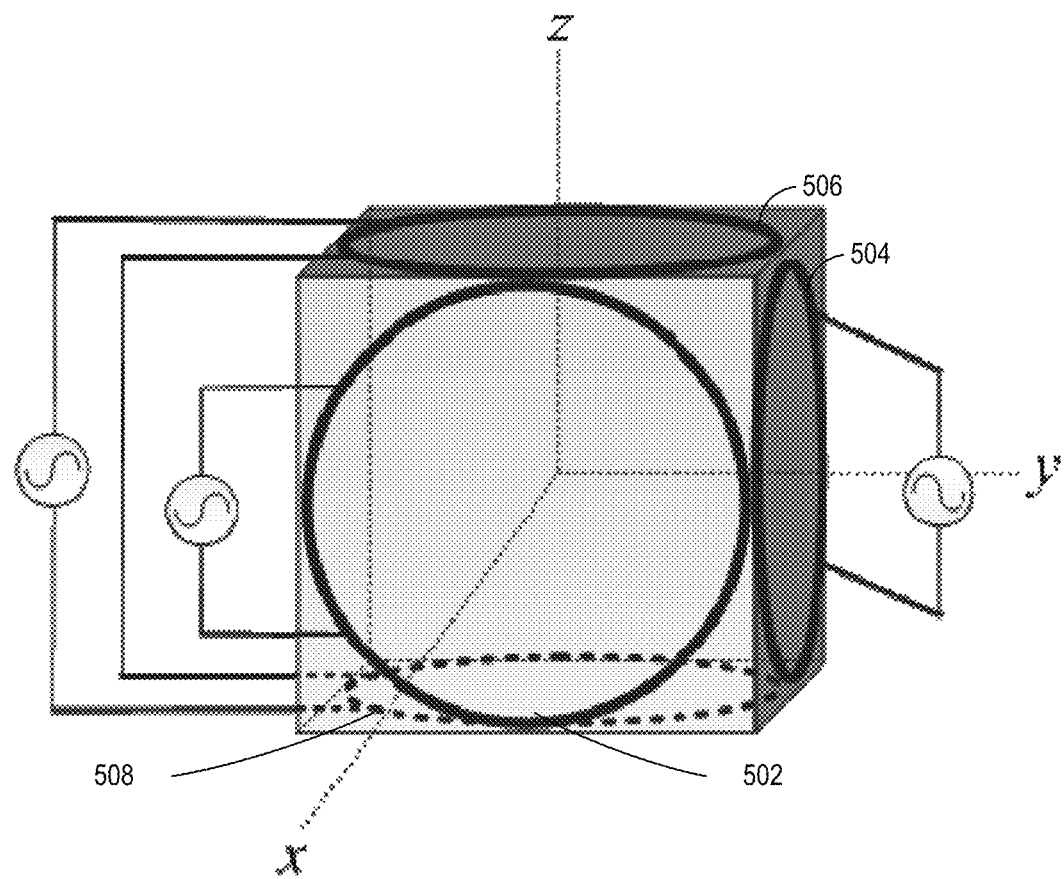
FIG. 5 illustrates another example arrangement of transmitting elements that can be included in a pill.

FIG. 5 illustrates another example arrangement of transmitting elements that can be included in a pill. In the illustrated example, there are two transmitting elements per axis (e.g. transmitting element 506 paired with 502). The corresponding pair for transmitting elements 502 and 504 are not shown in the figure. The transmitting elements can include a wire coil. In some embodiments, each pair of transmitting elements per axis can form a Helmholtz coil. The radius of each pair of coil can be same or substantially similar within 5% to 10%. In some embodiments, the radius of all the transmitting elements along each axis is the same or substantially similar. Each pair of coils, for example coils 502 and 506 may be separated by a distance that is approximately twice the radius of the coils. In some embodiments, the radius of a pair on one axis may be different compared to the radius of a second pair on a different axis. For example, a pair including coils 506 and 508 may be smaller in radius compared to a pair including coil 504 and its counterpart. Accordingly, the distance between the pairs may also vary. The distance may be limited by pill dimensions. In one embodiment, the coils in each pair are coaxial. The radius of the coils may also be a function of pill dimensions. Larger radius may generate larger magnetic fields.

In some embodiments, running a time-varying current through a pair of coils (e.g. 506 and 508) at the same or similar time can generate magnetic field in a direction perpendicular to the plane of the loops. For instance, the direction of the magnetic field may be parallel to the z-direction shown when a time-varying current is passed through coils 506 and 508. In some embodiments, the pair of coils can generate magnetic fields that are more uniform at a distance compared to a single coil. In some embodiments, the pair of coils (e.g. 506 and 508) may be electrically coupled. Further, the pair of coils can be separated by a ferrite core or other magnetic material or non-magnetic material. A ferrite core may enhance the generated magnetic field.

Accordingly, in some embodiments, the pill can include multiple transmitting elements per axis structure where the axes are orthogonal with respect to each other for generating nearly isotropic field. Some example embodiments including the multiple transmitting elements per axis structure are discussed more in detail below. The multiple transmitting elements per axis structures described below can be electrically connected with a circuit board or a flex circuit board in a pill as discussed above with respect to FIGS. 4A-B. In some embodiments, circuit boards may also mechanically support the multiple transmitting elements per axis structures. For example, circuit boards may include receiving adapters for connecting with the multiple transmitting elements per axis structures.

VIII. Bobbin Structure

Figure 6A:
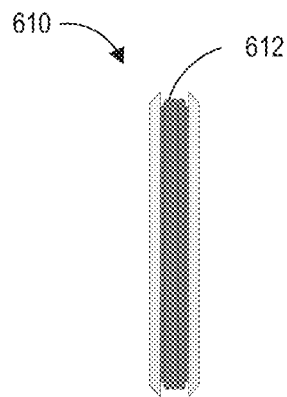
FIGS. 6A-D illustrate an embodiment of a multiple transmitting elements per axis structure using a bobbin design.
Figure 6B:
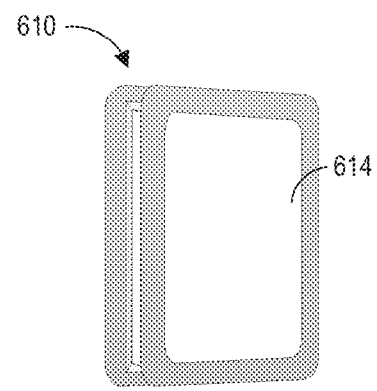

FIGS. 6A-D illustrate an embodiment of a multiple transmitting elements per axis structure using a bobbin design. In the illustrated embodiment, the transmitting elements include a wire coil. The wire coil can be composed using a 42 gauge (AWG) (or other size) copper wire. FIG. 6A illustrates a side view of an embodiment of a bobbin 610 with a wire 612 wrapped around a core of the bobbin in a coil. FIG. 6B illustrates a perspective view of the bobbin of FIG. 6A.

Figure 6C:
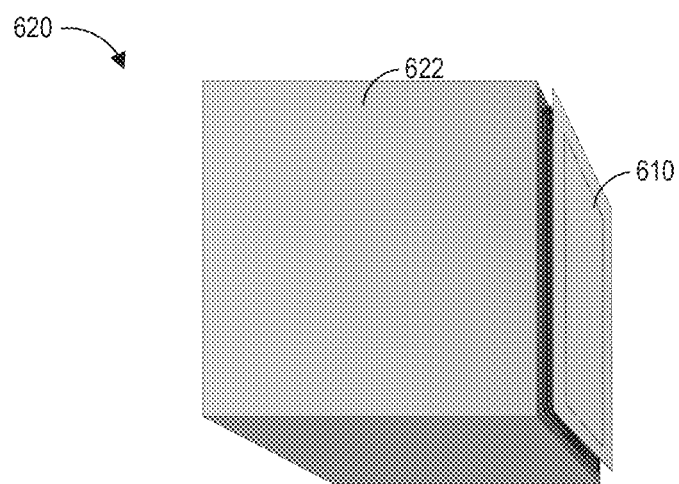

The bobbin 610 can be attached to a cube core 620. The bobbin can be made of a plastic material such as polyethylene. In some embodiments, the bobbin 610 can be attached with the cube core 620 as shown in FIG. 6C using an adhesive. For example, adhesive may be applied on the face 614 of the bobbin 610 and/or one of the faces 622 of the core 620. The face 614 of the bobbin 610 can then be affixed on to the face 622 of the core 620 using pressure. Accordingly, bobbins 610 including wire coils 612 can be affixed on to each of the faces 622 of the cube core 620 using adhesive or other suitable fastening mechanism. Other fastening mechanisms can include a Velcro, soldering, mechanical means (screws, nuts and bolts, etc.), or magnetic means. Bobbins 610 affixed on each side of the cube 620 can create a Helmholtz-type structure discussed above with respect to FIG. 5. Furthermore, the cube 620 can also include a ferrite core. While bobbins may be separately manufactured and affixed to a core, in some embodiments, the bobbins can also be carved out from a cube core.

In the bobbin structure, the windings of a coil do not overlap with windings of another coil as each winding has its own bobbin. At moderate frequencies (~10 MHz), the skin depth in Cu is less than typical wire diameters and if the coils overlapped, the signal from the underlying coil would not penetrate the overlying coil and the arrangement would prevent the signal from being transmitted outside of the pill.

Figure 6D:
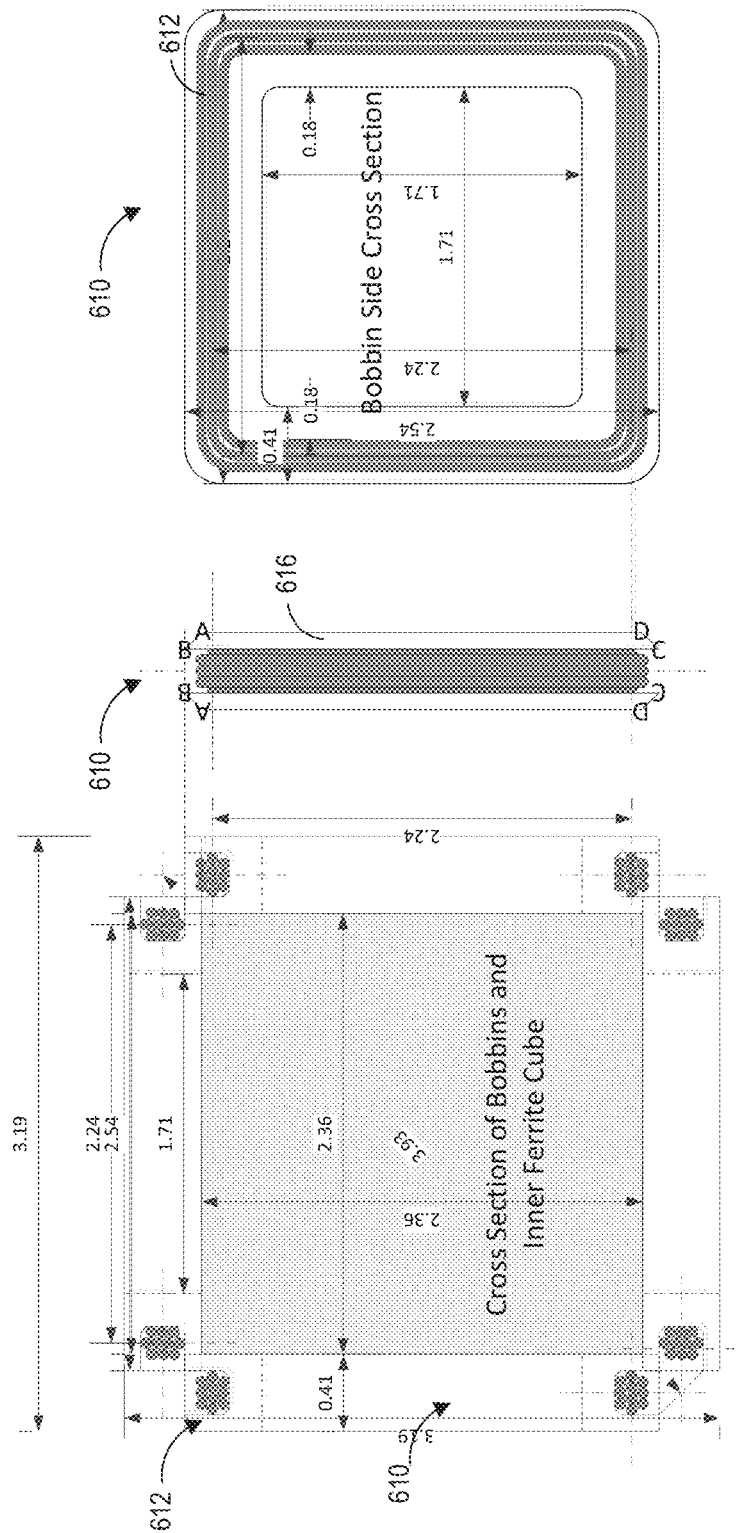

FIG. 6D illustrates multiple views of the bobbin-core structure. The example dimensions for the embodiment illustrated in FIG. 6 are in millimeters. The dimensions can vary based on the number of turns required for the wire coil and/or thickness of the wire. In one embodiment, there are 5 or less turns. In another embodiment, there are 20 or less turns.

The width of the bobbin wall 616 may also be a function of the number of turns of the wire coil 612. The edge of the bobbin wall 616 may be beveled at an angle so that the bobbin outer dimensions could exceed the dimensions of the cube 620. The extra dimension may be used to increase available area for the coil windings.

IX. PEG Design

Figure 7B:
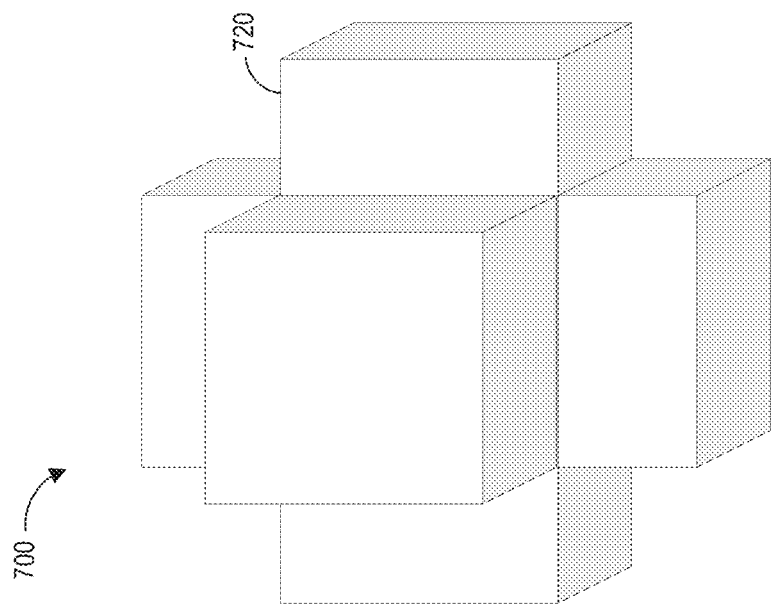
FIGS. 7A-B illustrate an embodiment of a multiple transmitting elements per axis structure 700 using a peg design.
Figure 7A:
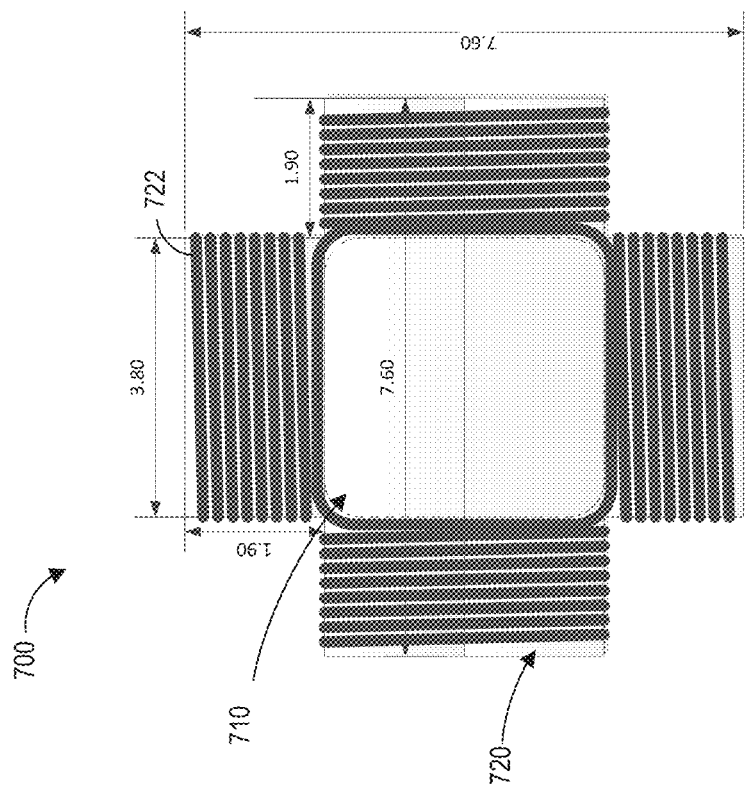

FIGS. 7A-B illustrate an embodiment of a multiple transmitting elements per axis structure 700 using a peg design. In the illustrated embodiment, the structure 700 includes a cubic core 710 with protrusions 720 extending from each face of the core 710. The core 710 can include magnetic material such as ferrite. A wire coil 722 can be wrapped around the protrusions 720. The length of the protrusions 720 extending from the face of the cube 710 can be a function of number or turns and the thickness of the wire. In one embodiment, the width of the protrusion is about 1.5 mm, although other sizes are possible. The protrusions 720 can be affixed using mechanical or magnetic means with the core 710. In some embodiments, the protrusions 720 can be carved out from a larger block such that the core 710 and the protrusions 720 are formed from a single piece. In the illustrated embodiment, there are two coils (transmitting elements) for each axis to form a Helmholtz-type structure discussed above with respect to FIG. 5. FIG. 7B illustrates a perspective view of the pill 700.

X. Spiral Design

Figure 8A:
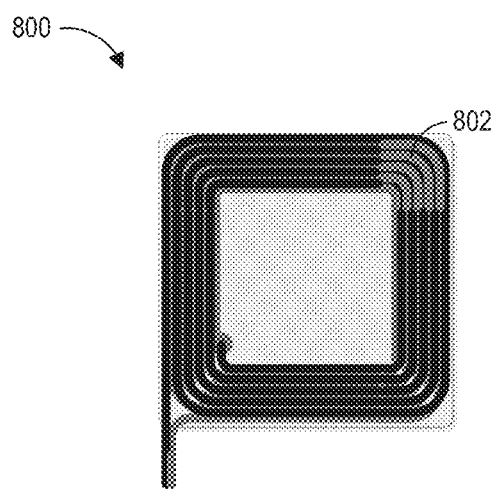
FIG. 8A illustrates an embodiment of a spiral face plate that can be used to create a multiple transmitting elements per axis structure.

FIG. 8A illustrates an embodiment of a spiral face plate 800 that can be used to create a multiple transmitting elements per axis structure. The face plate 800 can be a thin sheet of plastic or a thin sheet of plastic including ferrite. For example, the spiral pattern can be implemented with a flex-circuit, which may be a thin layer of copper bonded to a flexible substrate. The face plate 800 can include a spiral pattern of wire 800 on one or both sides of its surface. The spiral pattern of wire can include, for example, thin wire rods or copper wires. The spiral face plates 800 can be affixed to each side of a cube to create a multiple transmitting elements per axis structure. The cube can also include a ferrite core. In some embodiments, the spiral plates can be of different sizes to fit a rectangular prism structure.

Figure 8B:
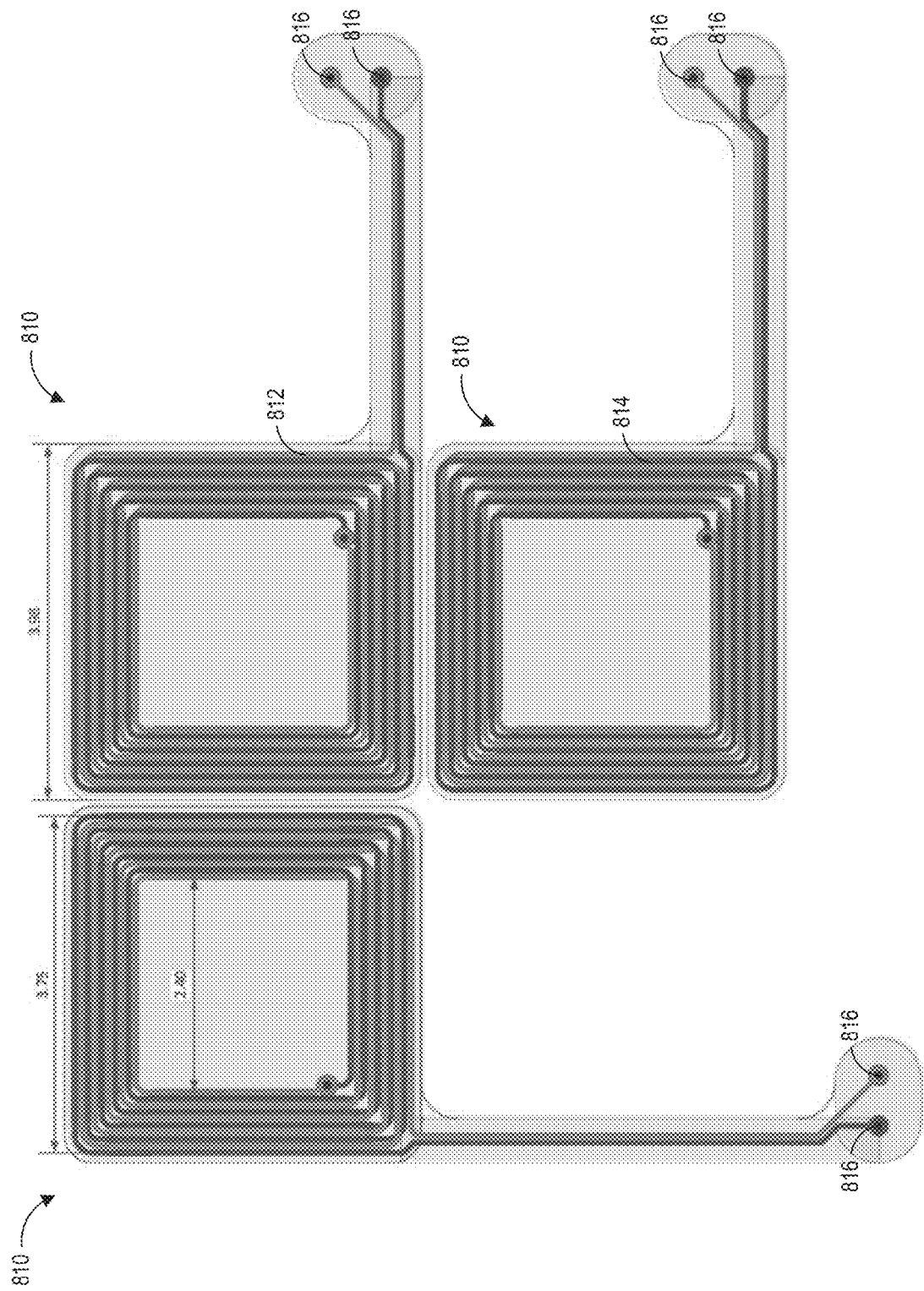
FIG. 8B illustrated another embodiment of a spiral face plate including spirals on both sides of the face plate.

Further, in some embodiments, three spiral face plates 810 as shown in FIG. 8B including spiral coils on both sides of its surfaces may be affixed to cover three faces of the cube in orthogonal directions. For example, a first conducting spiral element 812 can be formed on a first surface of the face plate 810 and a second conducting spiral element 814 can be formed on the second surface of the face plate 810. The first surface may be opposite from the second surface. The spiral conducting elements can be connected to contacts 816. In some embodiments, the contacts 816 may be provided on a circuit board as shown in FIG. 4A. The example dimensions illustrated in FIG. 8B are in millimeters. The dimensions of the spiral face plates may be a function of pill dimensions as discussed above.

The spiral face plates may also be manufactured by plating copper over a high resistivity ferrite and/or etching a copper pattern directly on the cube core.

XI. Notch Structure

FIGS. 9A-B illustrates an embodiment of a multiple transmitting elements per axis structure 900 using a notch design. To create the illustrated structure 900, notches or grooves 910 can be cut out from a cube or a rectangular prism. The depth of the notches 910 may depend on the number of turns and the thickness of the wire 912 that can be wrapped around the notches along each face of the cube or prism.

XII. Pill Circumference Design

FIG. 10 illustrates an embodiment a pill 1000 including wire coils 1002, 1004, and 1006 wrapped around the inner circumference of the pill coating. FIG. 10 shows a first coil 1002 wrapped inside the pill along the circumference of the pill coating. The first coil 1002 can be substantially parallel to a first major axis or the longitudinal axis of the pill 1000. The longitudinal axis can be parallel to the z-axis as shown in FIG. 10 To increase or attempt to maximize area of the first coil 1002, it can be wrapped about the major axis of the pill 1000 substantially parallel to the y-z plane. Further, in some embodiments, a second coil 1004 can be wrapped around a second major axis of the pill 1000 substantially parallel to the x-z plane. Wrapping the coil about the major axis may, in some embodiments, increase area of the coil.

The pill 1000 may also include a third coil 1006 that can be wrapped around the minor axis of the pill 1000. The minor axis can be parallel to the x-axis as shown. The third coil 1006 can be positioned at or near the center of the pill 1000. Since the area along on the minor axis may be smaller, in some embodiments, the third coil 1006 includes more turns than the first or the second coil.

The pill 1000 may include pill inner electronics that may interfere with the generated magnetic field. However, in some embodiments of the pill 1000, the large coil size relative to smaller electronics may be sufficient to overcome the interference.

XIII. Transmission Elements Design Parameters

When the transmitting elements are excited by a time-varying current, I at a frequency F, the magnetic field intensity can be proportional to $\omega \cdot I \cdot A \cdot N$, where $\omega = 2\eta F$, A is the effective area of the coil, and N is the total number of turns on the coil. In some embodiments, the pill's intended use and operating environment may impose constrains on the design parameters. For example, as discussed above, the size of the pill might be constrained based on a patient's comfort level of swallowing a pill or the diagnostic purpose of the pill, for motility variability considerations. Accordingly, the available area and battery power for current may be limited. The operating frequency may be limited because of concerns of tissue absorption. Also, the number of turns may be limited by size and available surface area of the pill. Accordingly, in the embodiments of the pills discussed above, the coil area, number of turns, and circulating coil current can increase generated signal from the transmitting elements.

XIV. Transmission Process

Figure 11:
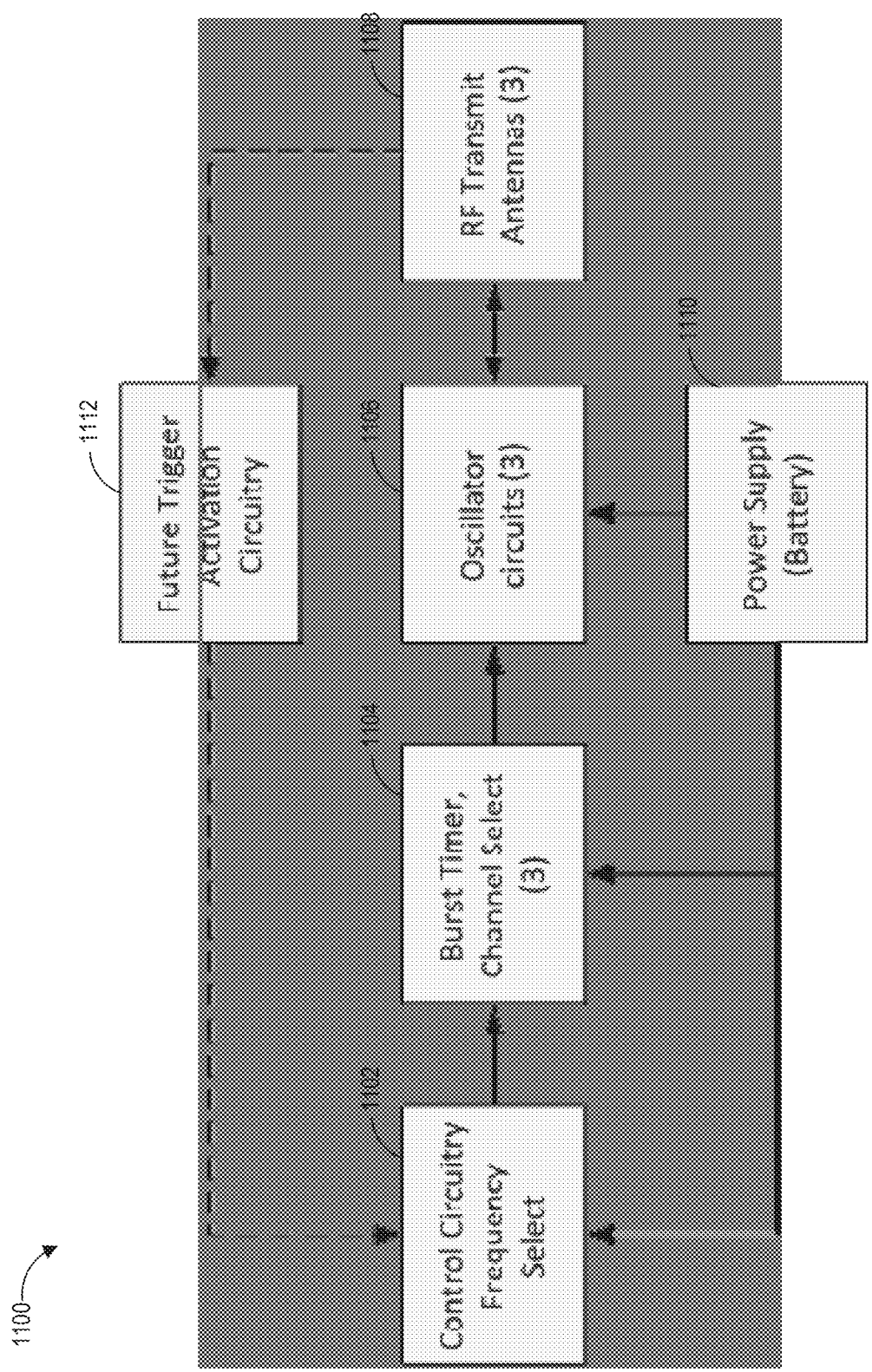
FIG. 11 illustrates a block diagram of an embodiment of a system 1100 including one or modules for generating magnetic field from multiple transmitting elements 1108.

FIGS. 3 to 10 illustrate various embodiments of pill transmitters including multiple transmitting elements. Further, the pills discussed above may include circuit elements to generate field from the transmitting elements. FIG. 11 illustrates a block diagram of an embodiment of a system 1100 including one or modules for generating magnetic field from multiple transmitting elements 1108. The power supply 1110 may provide power to the modules of the system 1110. The power supply 1110 may include a battery or may receive power from an external signal through inductive elements. The modules of the system 1100 are described more in detail below.

a. Control Module

The control module 1102 can include circuit elements for selecting an operating frequency for transmitting field from one or more of the transmitting elements 1108. Due to manufacturing and other design constraints, the transmitting elements in a pill may not be completely orthogonal with respect to each other. This may result in some non-zero cross coupling between transmitting elements. Accordingly, in some embodiments, the control circuit 1102 can select different operating frequencies for each of the transmitting elements to minimize cross-talk. The frequencies may differ by about 5% to 10% (or more or less) between each of the transmitting elements. For example, the control module 1102 can select a frequency of 9 MHz for a first transmitting element, 10 MHz for a second transmitting element, and 11 MHz for a third transmitting element. In some embodiments, the frequencies may differ by less than 5% or more than 10%. The control module 1102 may also select identical frequencies for some or all of the transmitting elements.

The control module 1102 may include a memory for storing predetermined frequency patterns. The control module 1102 can also include a hardware processor for determining frequency patterns. In some embodiments, the control module 1102 may select frequency patterns based on an external input. For example, the input may be received via a mechanical switch or a wired or wireless signal. The control module 1102 can also include a processor programmed with executable instructions to select frequency. Accordingly, the control module 1102 can include preprogrammed logic patterns or circuits to determine output frequency.

b. Timer Module

The timer module 1104 can control the time of operation and accordingly the duty cycle of the transmitting elements. In some embodiments, the timer module 1104 can sequentially activate each of the transmitting elements. Using the embodiment discussed in FIG. 4 an example, the timer module 1104 can activate transmitting element 402 for a first time period while transmitting elements 404 and 406 are off, then transmitting element 404 for a second time period while transmitting elements 402 and 406 are off, and transmitting element 406 for a third time period while transmitting elements 402 and 404 are off. The order may vary between embodiments. The first, second, and third time periods may all be the same or vary depending on design parameters. For example, the third time period corresponding to the transmitting element 402 may be longer than the first and second time period to account for additional interference facing transmitting element 402. In some embodiments, the time period may be longer for transmission in the majority orientation (e.g. transmitting elements 404 and 406). In one embodiment, the time period is 16 ms. In some embodiments, a receiver antenna positioned proximate to the body of a patient experiences at least half-maximum field for at least $\Delta t$ when each of the transmitting elements are activated for a particular time period, $\Delta t$.

As discussed above, in some embodiments, the operation of the transmitting elements may not overlap in time. The timer module 104 may implement a delay between activation of each of the transmitting elements. In some embodiments, there is no delay between activation of each of the transmitting elements. For example, the timer module can also activate multiple transmitting elements at the same time to operate the multiple transmitters as a phased array.

In some embodiments, each cycle includes a transmission from each of the transmitting elements of a pill for a time period. The timer module 1104 can the time between each cycle. The time between each cycle may depend on available battery or in some instances the speed of movement of the pill transmitter. In one embodiment, the time between each cycle is one second. The timer module 1102 can also include a processor programmed with executable instructions to select time period and cycle period.

c. Oscillator Circuit

The system 1100 can include one or more oscillator circuits 1106 to drive the transmitting elements. In some embodiments, there may multiple oscillator circuits 1106 corresponding to different frequencies. Some oscillator circuit 1106 can include transistors to select one or more of the resistors, capacitors, or inductive elements to tune the frequency of a particular transmitting element. For the embodiments of pill including two transmitting elements per axis, the oscillator circuit can be configured as a Hartley oscillator. Further, in some embodiments, the oscillator circuit 1106 can form a resonant tank circuit. The control circuit 110 can select one of the oscillator circuits 1106 to transmit field from one of the transmitting elements.

d. Future Trigger Activation Module

In some embodiments, the system 1100 can also include future trigger activation module 1112. The future trigger activation module 1112 can activate the next cycle of transmission from the transmitting elements. The future trigger activation module 1112 can receive an external trigger to activate the next cycle or may include a timing circuit to vary the sequence and or duration of pulsed emission.

XV. Calculating Pill Positions

Figure 12:
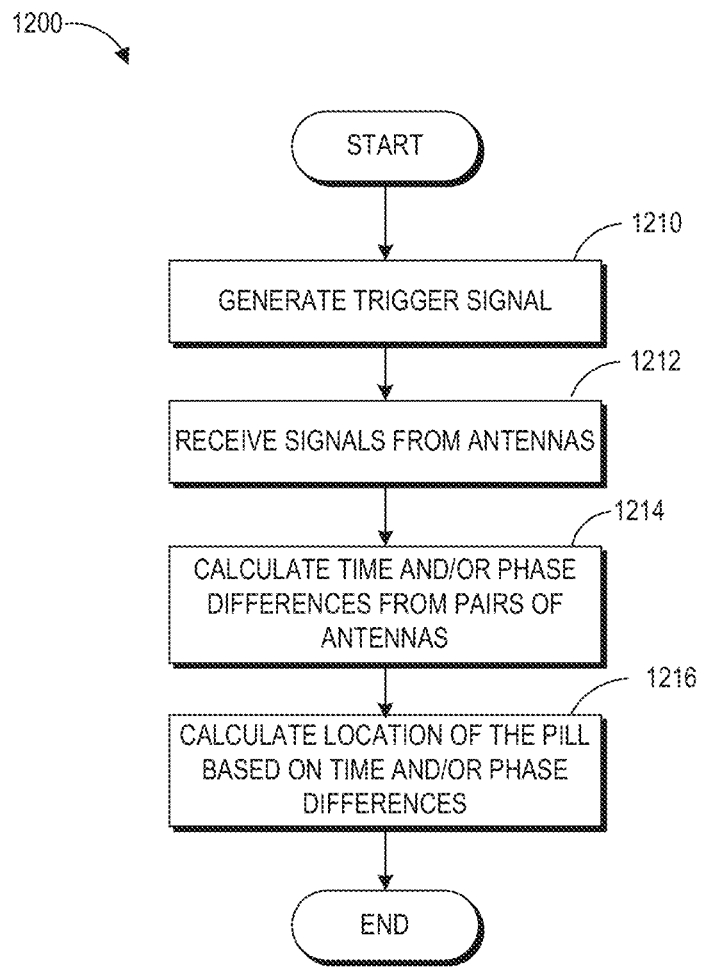
FIG. 12 illustrates an embodiment of a process for calculating the location of a pill transmitter.

FIG. 12 illustrates an embodiment of a process 1200 for calculating the location of a pill in the patient 12. This process can be implemented by the system 100 described herein. In particular, each of these processes can be implemented by one or modules in the patient monitor 20 described above. Advantageously, in certain embodiments, these processes can enable monitoring of a pill as it moves through the GI tract of a patient. In some embodiments, the location of the TUs and the coupling coefficients between the antennas are calculated prior to calculating the location of the pill.

Referring specifically to FIG. 12, at block 1210, the signal generator module 154 can generate a trigger signal that may be transmitted from an external stimulus antenna 18. The pill 14 can receive the trigger signal and in response transmit one or more signal waveforms from one or more transmitting elements as discussed above. The plurality of TUs or receiver antennas 16 can receive the signal waveform transmitted from the pill 14. In some embodiments, the receiver antennas 16 include a flat round coil. The coil may be flexible. In one embodiment, the receive coil is 2 inches in diameter. In some embodiments, where the pill includes three transmitting elements in orthogonal directions, it is likely that a receiving antenna may experience flux from at least one of the transmitting elements.

In some embodiments, the pill 14 can generate the transmit signal without requiring a trigger signal. At block 1212, the signal collector module 162 can collect the received signal waveforms from the plurality of TUs 16. In some embodiments, the signal collector module 162 may select only the strongest signal received from each of the receiver antennas. In some embodiments, the calculator module 152 can calculate locations based on two or more received signals in each cycle from respective transmitting elements. For instance, the calculator module 152 can calculate a first location based on the received signal from the first transmitting element and a second location based on the received signal from the second transmitting element. The calculator module 152 can then average the two location estimates or pick one based on tracking.

The calculator module 152 can analyze the collected waveforms to calculate a first set of measurements at block 1214. In an embodiment, the measurement module of the patient monitor 20 can calculate relative phase (or phase shifts) and amplitude measurements for each of the collected signals. In certain embodiments, the measurement module can also measure the phase differences between one or more pairs of collected signals. Then, at block 1216, the location calculator module can calculate the location of the pill by applying a first set of rules, analysis, or filtering on the measurements.

The first set of rules can include linear, non-linear, or a combination of linear and non-linear set of operations. In an embodiment, the first set of rules can be applied to an electromagnetic coupling model of the system described more in detail in application Ser. No. 13/969,435. In certain embodiments, an estimator module 158 can calculate a first estimate of the pill location. The location calculator module 152 can use the first estimate as a starting set of values to solve for the location of the pill. For example, in certain embodiments, a linear set of operations (e.g. multivariate linear regression) can be used to calculate the location estimate and then the location calculator module can use non-linear operations (e.g. Levenberg-Marquart analysis) to refine the estimated value. As the pill moves through the body, location state vector models may be used to further improve the accuracy of tracking. For example, a Markov chain, Kalman filter, or a combination of Markov chain and Kalman filters can be used to improve tracking. Other tracking filters may also be used. A pill trajectory can be calculated by taking derivative of the pill locations. The trajectory may be shown on the display 30.

The location calculator module 152 can use one or more models to calculate the location of the pill. For example, the calculator module 152 can use electromagnetic coupling model which is described more in detail in application Ser. No. 13/969,435. The location calculator module can also use multilateration analysis on the collected signals for calculating pill locations. The multilateration analysis can be used independently or in conjunction with the electromagnetic coupling model. The location calculator module 152 can take into account secondary coupling effects described below to refine the measurements. In some embodiments, the pill can be accurately located within a 1 cm error margin in three dimensions.

In some embodiments, the location calculator module 152 can calibrate the system by measuring initial system parameters for use in one or more model calculations. The system parameters can include pill geometry, location of the TUs, orientation of the TUs, and other related inherent properties of the system. The location calculator module can apply the system parameters in calculating the location of the pill. Further, dynamic calibration can modify the initial system parameters by automatically measuring the location of TUs over time as described below.

A detailed description on calculating pill location is further described in a related application Ser. No. 13/969, 435. In some embodiments, the calculations for pill location may take less than 1 second or less than 2 second.

Figure 13:
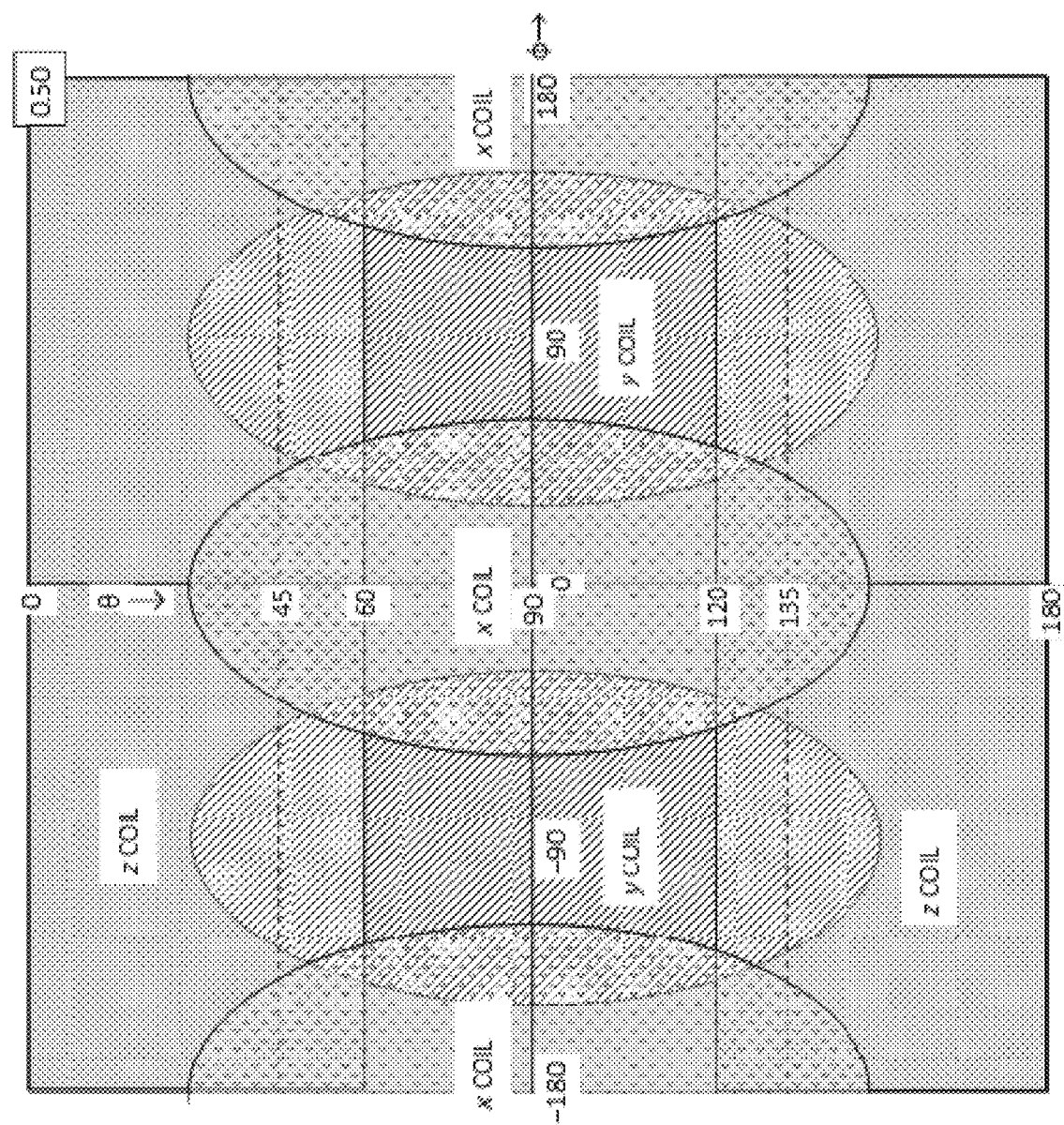
FIG. 13 illustrates a model of transmitted magnetic field from a model three transmitting elements structure.

FIG. 13 illustrates an example model of transmitted magnetic field from a model of three transmitting elements. The radial field component in this example exceeds ½ maximum out to 60° off axis. The areas of the sphere that experience at least ½ maximum $B_r$ from each coil (the x-directed, or y-directed, or z-directed coil) in the time-sharing scheme are shown in FIG. 13. The entire sky sphere is covered in this example. The areas that experience at least ¾ maximum $B_r$ from each coil turn out to cover ¾ of the sphere in this example. The example model of FIG. 13 can illustrate at least some of the near-isotropic benefits that may be derived from certain embodiments disclosed herein.

XVI. Additional Embodiments

While the embodiments discussed above illustrate a pill transmitter that can be swallowed by a patient, the structures disclosed herein can be used in transmitters for locating other objects. For example, the transmitters can be used to tags products, inventory, or industrial applications to improve signal reception by such systems. The antennas described herein can also be used in systems or devices that transmit in the traditional AM radio, FM radio, RFID, or other low frequency or signal communications bands that range from 1 kHz to over 100 MHz. The antennas described herein can be used in systems or devices that transmit in the traditional cellular phone communications bands to improve handset reception by removing the directionality of digital and analog data from cellular systems. The antennas described herein can be used in inductively coupled charging systems, such as in cellular phones, handheld equipment, and other instrumentation, in order to improve coupling effectiveness when the instrument charging circuitry is not optimally aligned with the inductive coupling charging system.

TERMINOLOGY

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated.

Furthermore, it should be understood when referring to direction of magnetic field or signals, it does not necessarily mean that there is no magnetic field outside of the axis of transmission. Thus, when direction of magnetic the field is discussed with respect to transmitting elements, it may be in relation to where a receiving element may experience highest magnetic field.

The term "substantially parallel," when used to describe two axes or planes, in addition to having its ordinary meaning, may refer to an angle between a first and a second axis (or plane) that is 0 degrees, less than or equal to 1 degree, a few degrees, or less than or equal to some other small value, such as 10 or 15 degrees. Furthermore, the terms "substantially orthogonal" or "substantially perpendicular," when used to describe two axes or planes, in addition to having their ordinary meaning, may refer to an angle between a first and a second axis (or plane) that is 90 degrees or that is between 75 and 105 degrees, that is between 80 and 100 degrees, that is between 85 and 95 degrees, that is between 89 and 91 degrees, or that is otherwise close to 90 degrees or within some small variance from 90 degrees.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, a smartphone, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

Additionally, terms such as "above," "below," "top," and "bottom" are used throughout the specification. These terms should not be construed as limiting. Rather, these terms are used relative to the orientations of the applicable figures.

What is claimed is:

1. A system for locating a patient-swallowed pill transmitter, the system comprising:
    a swallowable-pill transmitter comprising:
    a flexible circuit board;
    a cube ferrite core;
    a first face plate comprising a first transmitting element arranged in a first coil on a first surface of the first face plate, the first transmitting element electrically coupled with the flexible circuit board, said first transmitting element configured to transmit a first signal in a first axis substantially perpendicular to a longitudinal axis of the pill transmitter;
    a second face plate comprising a second transmitting element arranged in a second coil on a second surface of the second face plate, the second transmitting element electrically coupled with the flexible circuit board, said second transmitting element configured to transmit a second signal in a second axis substantially perpendicular to the longitudinal axis of the pill transmitter and substantially perpendicular to the first axis;
    a third face plate comprising a third transmitting element arranged in a third coil on a third surface of the third face plate, the third transmitting element electrically coupled to the flexible circuit board, said third transmitting element configured to transmit a third signal in a third axis substantially parallel to the longitudinal axis of the pill transmitter,
    wherein the third face plate is located on a first end of the flexible circuit board, and
    wherein the first face plate is configured to wrap on a first side of the cube ferrite core, the second face plate is configured to wrap on to a second side of the cube ferrite core, and the face plate is configured to wrap on to a third side of the cube ferrite core; and
    a battery positioned on a second end of the flexible circuit board,
    wherein the second end is opposite the first end of the flexible circuit board,
    wherein the battery is separated by a distance from the third face plate spanning the longitudinal axis of the pill transmitter, and said third transmitting element is arranged farther away from the battery compared to the first transmitting element and the second transmitting element to increase an angle of field leaving the swallowable-pill transmitter, and
    wherein the battery is configured to be positioned on the flexible circuit board such that the battery does not intersect with the first axis and the second axis.

2. The system of claim 1, wherein a longitudinal axis of the circuit board is substantially parallel to the longitudinal axis of the pill.

3. The system of claim 1, wherein said third transmitting element is positioned on a side opposite from said first transmitting element with respect to the circuit board.

4. The system of claim 1, wherein said third transmitting element is positioned on a first surface of the circuit board opposite from a second surface of the circuit board, second surface including said first and second transmitting elements.

5. The system of claim 1, wherein said third transmitting element is positioned on a side opposite from said second transmitting element with respect to the circuit board.

6. The system of claim 1, further comprising a plurality of circuit elements positioned on the circuit board such that the plurality of circuit elements do not intersect with at least one of the first axis or the second axis.

7. The system of claim 6, wherein the circuit elements are positioned on a surface of the circuit board opposite from a surface of the circuit board electrically coupling said first and second transmitting element.

8. The system of claim 1, further comprising a plurality of receivers configured to receive transmitted signals from at least one of the first, second, or third transmitting elements.

9. The system of claim 8, wherein the plurality of receivers comprise a flat coil.

10. The system of claim 8, further comprising a patient monitor configured to calculate a position of the pill transmitter based on the received signals.

11. The system of claim 1, further comprising a timing module configured to set a time period for operation of said first, second, and third transmitting elements.

12. The system of claim 1, further comprising a control module configured to select an operating frequency for each of the first, second, and third transmitting elements.

13. The system of claim 1, wherein the first face plate is wrapped on the first side of cube ferrite core with an adhesive.

14. The system of claim 1, wherein the first transmitting element is configured to transmit the first signal in response to an external trigger signal.

* * * * *